(12) United States Patent  
Kalpin et al.

(10) Patent No.: US 9,044,537 B2
(45) Date of Patent: Jun. 2, 2015

(54) DEVICES AND METHODS FOR DETECTING CATHETER COMPLICATIONS

(75) Inventors: Scott L. Kalpin, Harris, MN (US); Lucien Bell Solefack, South St. Paul, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 822 days.

(21) Appl. No.: 13/169,092

(22) Filed: Jun. 27, 2011

(65) Prior Publication Data

US 2011/0257593 A1    Oct. 20, 2011

Related U.S. Application Data

(63) Continuation-in-part of application No. 11/731,356, filed on Mar. 30, 2007, now Pat. No. 8,323,244.

(51) Int. Cl.
*A61M 25/00* (2006.01)
*A61M 5/142* (2006.01)
(Continued)

(52) U.S. Cl.
CPC ....... *A61M 5/14276* (2013.01); *A61M 5/16854* (2013.01); *A61M 5/16859* (2013.01); *A61M 5/1723* (2013.01); *A61M 27/006* (2013.01); *A61M 2005/1726* (2013.01); *A61M 2202/0464* (2013.01); *A61M 2205/3331* (2013.01);
(Continued)

(58) Field of Classification Search
CPC ..................... A61M 5/14276; A61M 5/16831; A61M 5/16854; A61M 5/16863
USPC ......... 600/485, 486; 356/39; 604/111, 65, 67, 604/93.01, 264, 523
See application file for complete search history.

(56) References Cited

U.S. PATENT DOCUMENTS

| 3,882,443 A | 5/1975 | Mortia |
| 4,137,913 A | 2/1979 | Georgi |

(Continued)

FOREIGN PATENT DOCUMENTS

| EP | 0 248 632 | 12/1987 |
| EP | 0 248 633 | 12/1987 |

(Continued)

OTHER PUBLICATIONS

U.S. Appl. No. 12/623,484, filed Nov. 23, 2009.
(Continued)

*Primary Examiner* — Laura Bouchelle
(74) *Attorney, Agent, or Firm* — Mueting, Raasch & Gebhardt, P.A.

(57) ABSTRACT

A method for determining status of an implanted catheter includes acquiring raw pressure data from a pressure sensor of in an implantable infusion device. The pressure sensor is in communication with a lumen of the catheter operably coupled to the infusion device. The catheter has a delivery region, in communication with the lumen, intended to be positioned in a fluid-filled target location of a patient. The method further includes filtering the raw pressure data to remove the DC component, leaving the AC component within a relevant physiological frequency range; rectifying the AC component to produce a rectified pressure signal; calculating a mean magnitude of the rectified signal; and determining whether the mean magnitude is below a predetermined threshold. If the mean magnitude is below the threshold, the catheter is determined to be in a state other than a normal state.

19 Claims, 22 Drawing Sheets

(51) Int. Cl.
*A61M 5/168* (2006.01)
*A61M 5/172* (2006.01)
*A61M 27/00* (2006.01)

(52) U.S. Cl.
CPC .............. *A61M2205/3344* (2013.01); *A61M 2205/3355* (2013.01); *A61M 2210/0693* (2013.01); *A61M 2230/005* (2013.01); *A61M 2230/04* (2013.01); *A61M 2230/06* (2013.01); *A61M 2230/40* (2013.01); *A61M 2230/42* (2013.01); *A61M 2230/63* (2013.01)

(56) References Cited

U.S. PATENT DOCUMENTS

| | | | | |
|---|---|---|---|---|
| 4,373,527 | A | 2/1983 | Fischell | |
| 4,388,833 | A | 6/1983 | Kuwayama | |
| 4,530,696 | A | 7/1985 | Bisera | |
| 4,534,756 | A | 8/1985 | Nelson | |
| 4,551,133 | A | 11/1985 | Zegers de Beyl | |
| 4,619,653 | A | 10/1986 | Fischell | |
| 4,710,163 | A | 12/1987 | Butterfield | |
| 4,714,462 | A | 12/1987 | DiDomenico | |
| 4,784,645 | A | 11/1988 | Fischell | |
| 4,979,940 | A | 12/1990 | Bobo, Jr. | |
| 5,006,997 | A | 4/1991 | Reich | |
| 5,024,668 | A | 6/1991 | Peters | |
| 5,040,536 | A | 8/1991 | Riff | |
| 5,059,171 | A | 10/1991 | Bridge | |
| 5,078,682 | A | 1/1992 | Miki | |
| 5,087,245 | A | 2/1992 | Doan | |
| 5,096,385 | A | 3/1992 | Georgi | |
| 5,116,203 | A | 5/1992 | Natwick | |
| 5,158,547 | A | 10/1992 | Doan | |
| 5,176,631 | A | 1/1993 | Koenig | |
| 5,190,522 | A | 3/1993 | Wojcicki | |
| 5,205,819 | A | 4/1993 | Ross | |
| 5,207,666 | A | 5/1993 | Idriss | |
| 5,276,610 | A | 1/1994 | Maeda | |
| 5,279,544 | A | 1/1994 | Gross | |
| 5,290,231 | A | 3/1994 | Marcadis | |
| 5,328,460 | A | 7/1994 | Lord | |
| 5,336,181 | A | 8/1994 | Nakao | |
| 5,342,298 | A | 8/1994 | Michaels | |
| 5,356,378 | A | 10/1994 | Doan | |
| 5,496,273 | A | 3/1996 | Pastrone | |
| 5,501,665 | A | 3/1996 | Jhuboo | |
| 5,535,752 | A | 7/1996 | Halperin | |
| 5,560,366 | A * | 10/1996 | Harada et al. | 600/494 |
| 5,605,545 | A | 2/1997 | Nowosielski | |
| 5,609,576 | A | 3/1997 | Voss | |
| 5,645,734 | A | 7/1997 | Kenley | |
| 5,669,877 | A | 9/1997 | Blomquist | |
| 5,695,473 | A | 12/1997 | Olsen | |
| 5,800,387 | A | 9/1998 | Duffy | |
| 5,827,223 | A | 10/1998 | Butterfield | |
| 5,853,386 | A | 12/1998 | Davis | |
| 5,893,838 | A | 4/1999 | Daoud | |
| 5,899,873 | A | 5/1999 | Jones | |
| 5,906,589 | A | 5/1999 | Gordon | |
| 5,928,195 | A | 7/1999 | Malamud | |
| 5,935,106 | A | 8/1999 | Olsen | |
| 6,152,898 | A | 11/2000 | Olsen | |
| 6,203,523 | B1 | 3/2001 | Haller | |
| 6,213,972 | B1 | 4/2001 | Butterfield | |
| 6,223,081 | B1 * | 4/2001 | Kerver | 607/17 |
| 6,241,704 | B1 | 6/2001 | Peterson | |
| 6,358,225 | B1 | 3/2002 | Butterfield | |
| 6,364,842 | B1 * | 4/2002 | Amano et al. | 600/485 |
| 6,394,986 | B1 | 5/2002 | Millar | |
| 6,423,029 | B1 | 7/2002 | Eisberry | |
| 6,423,035 | B1 | 7/2002 | Das | |
| 6,458,102 | B1 | 10/2002 | Mann | |
| 6,464,687 | B1 | 10/2002 | Ishikawa | |
| 6,485,465 | B2 | 11/2002 | Moberg | |
| 6,551,290 | B1 | 4/2003 | Elsberry | |
| 6,609,071 | B2 | 8/2003 | Shapiro | |
| 6,620,151 | B2 | 9/2003 | Blischak | |
| 6,648,821 | B2 | 11/2003 | Lebel | |
| 6,716,193 | B1 | 4/2004 | Neftel | |
| 6,740,059 | B2 | 5/2004 | Flaherty | |
| 6,742,999 | B1 | 6/2004 | Nusser | |
| 6,966,325 | B2 | 11/2005 | Erickson | |
| 7,022,116 | B2 | 4/2006 | Morris | |
| 7,054,782 | B2 | 5/2006 | Hartlaub | |
| 7,092,797 | B2 | 8/2006 | Gaines | |
| 7,104,763 | B2 | 9/2006 | Bouton | |
| 7,118,565 | B2 | 10/2006 | Abboud | |
| 7,255,680 | B1 | 8/2007 | Gharib | |
| 7,255,683 | B2 | 8/2007 | Vanderveen | |
| 7,291,126 | B2 | 11/2007 | Shekalim | |
| 7,311,693 | B2 | 12/2007 | Shekalim | |
| 7,320,676 | B2 | 1/2008 | Miesel | |
| 7,338,464 | B2 | 3/2008 | Blischak | |
| 7,437,644 | B2 | 10/2008 | Ginggen | |
| 7,452,190 | B2 | 11/2008 | Bouton | |
| 7,505,869 | B2 | 3/2009 | Hartlaub | |
| 7,621,878 | B2 | 11/2009 | Ericson | |
| 7,722,574 | B2 | 5/2010 | Toman | |
| 7,763,007 | B2 | 7/2010 | Miesel | |
| 7,998,111 | B2 | 8/2011 | Moberg | |
| 2001/0034502 | A1 | 10/2001 | Moberg | |
| 2002/0040208 | A1 | 4/2002 | Flaherty | |
| 2002/0065471 | A1 * | 5/2002 | Amano et al. | 600/485 |
| 2002/0072733 | A1 | 6/2002 | Flaherty | |
| 2002/0077581 | A1 | 6/2002 | Davidner | |
| 2002/0087115 | A1 | 7/2002 | Hartlaub | |
| 2002/0107477 | A1 | 8/2002 | Kipfer | |
| 2002/0120236 | A1 | 8/2002 | Diaz | |
| 2002/0173773 | A1 | 11/2002 | Olsen | |
| 2003/0073954 | A1 | 4/2003 | Moberg | |
| 2003/0078547 | A1 | 4/2003 | Shekalim | |
| 2003/0088238 | A1 | 5/2003 | Poulsen | |
| 2003/0125662 | A1 | 7/2003 | Bui | |
| 2003/0135154 | A1 | 7/2003 | Heiniger | |
| 2003/0236489 | A1 | 12/2003 | Jacobson | |
| 2004/0034331 | A1 | 2/2004 | Toman | |
| 2004/0044305 | A1 | 3/2004 | Hughett | |
| 2004/0085215 | A1 | 5/2004 | Moberg | |
| 2004/0087894 | A1 | 5/2004 | Flaherty | |
| 2004/0097813 | A1 * | 5/2004 | Williams | 600/485 |
| 2004/0127844 | A1 | 7/2004 | Flaherty | |
| 2004/0220548 | A1 | 11/2004 | Heruth | |
| 2004/0230125 | A1 * | 11/2004 | Amano et al. | 600/485 |
| 2004/0260233 | A1 | 12/2004 | Garibotto | |
| 2004/0260234 | A1 | 12/2004 | Srinivasan | |
| 2005/0075624 | A1 | 4/2005 | Miesel | |
| 2005/0090799 | A1 | 4/2005 | Morris | |
| 2005/0123420 | A1 | 6/2005 | Richter | |
| 2005/0148885 | A1 * | 7/2005 | Tweed et al. | 600/490 |
| 2005/0192529 | A1 | 9/2005 | Butterfield | |
| 2005/0209512 | A1 | 9/2005 | Heruth | |
| 2005/0209513 | A1 | 9/2005 | Heruth | |
| 2005/0222643 | A1 | 10/2005 | Heruth | |
| 2005/0234514 | A1 | 10/2005 | Heruth | |
| 2005/0234518 | A1 | 10/2005 | Heruth | |
| 2005/0241387 | A1 | 11/2005 | Miesel | |
| 2005/0245858 | A1 | 11/2005 | Miesel | |
| 2005/0267413 | A1 | 12/2005 | Wang | |
| 2006/0042632 | A1 | 3/2006 | Bishop | |
| 2006/0060190 | A1 * | 3/2006 | Sinderby | 128/200.14 |
| 2006/0079793 | A1 * | 4/2006 | Mann et al. | 600/486 |
| 2006/0161376 | A1 | 7/2006 | Hartlaub | |
| 2006/0184154 | A1 | 8/2006 | Moberg | |
| 2006/0271029 | A1 | 11/2006 | Abboud | |
| 2006/0276744 | A1 | 12/2006 | Falk | |
| 2006/0282040 | A1 | 12/2006 | Toman | |
| 2007/0060871 | A1 | 3/2007 | Istoc | |
| 2007/0078381 | A1 | 4/2007 | Yap | |
| 2007/0149926 | A1 | 6/2007 | Moberg | |
| 2007/0191770 | A1 | 8/2007 | Moberg | |
| 2007/0232936 | A1 * | 10/2007 | Mann et al. | 600/486 |
| 2007/0244469 | A1 | 10/2007 | Ozeri | |
| 2007/0258083 | A1 * | 11/2007 | Heppell et al. | 356/39 |

(56) References Cited

U.S. PATENT DOCUMENTS

| | | |
|---|---|---|
| 2007/0270782 A1 | 11/2007 | Miesel |
| 2007/0274843 A1 | 11/2007 | Vanderveen |
| 2008/0009837 A1 | 1/2008 | Miesel |
| 2008/0097287 A1 | 4/2008 | Nelson |
| 2008/0139996 A1 | 6/2008 | Bowman |
| 2008/0167641 A1 | 7/2008 | Hansen |
| 2008/0221522 A1 | 9/2008 | Moberg |
| 2008/0221523 A1 | 9/2008 | Moberg |
| 2008/0243074 A1 | 10/2008 | Miesel |
| 2009/0082757 A1 | 3/2009 | Rogers |
| 2010/0016918 A1 * | 1/2010 | Mann et al. ............ 607/23 |
| 2010/0037680 A1 | 2/2010 | Moberg |
| 2010/0069841 A1 | 3/2010 | Miesel |
| 2011/0077605 A1 | 3/2011 | Karpowicz |

FOREIGN PATENT DOCUMENTS

| | | |
|---|---|---|
| EP | 0 328 162 | 8/1989 |
| EP | 328163 A2 * | 8/1989 |
| EP | 0 522 527 | 12/1994 |
| EP | 0 621 791 | 8/2000 |
| EP | 1 342 481 | 9/2003 |
| EP | 1 535 637 | 6/2005 |
| EP | 0 993 268 | 11/2005 |
| EP | 1 839 695 | 10/2007 |
| EP | 1 592 468 | 9/2008 |
| WO | WO 95/32013 | 11/1995 |
| WO | WO 99/55225 | 11/1999 |
| WO | WO 00/44420 | 8/2000 |
| WO | WO 02/064040 | 8/2002 |
| WO | WO 02/070047 | 9/2002 |
| WO | WO 2005/072792 | 8/2005 |
| WO | WO 2005/089860 | 9/2005 |
| WO | WO 2005/119181 | 12/2005 |
| WO | WO 2006/067217 | 6/2006 |
| WO | WO 2006/108775 | 10/2006 |
| WO | WO 2007/020029 | 2/2007 |

OTHER PUBLICATIONS

U.S. Appl. No. 11/731,355, filed Mar. 30, 2007.
U.S. Appl. No. 11/778,400, filed Jul. 16, 2007.
The SynchroMed Pump, datasheet, [online]. Medtronic, Inc., Minneapolis, MN, Version b3.01, [retrieved on Oct. 19, 2007]. Retrieved from the Internet:,URL:http://www.medtronic.com/neuro/paintherapies/pain_treatment_ladder/drug_infusion/umpumps_pump_sel/synchromed_pumps.html>; 4 pgs.
Geipel et al., "Design of an Implantable Active Microport System for Patient Specific Drug Release", Proceedings of the 24$^{th}$ IASTED International Multi-Conference on Biomedical Engineering (The International Association of Science and Technology for Development), Feb. 15-17, 2006, Innsbruck, Austria; pp. 161-166.
International Preliminary Report and Written Opinion on Patentability for PCT/US2008/057792; 8 pgs.
International Search Report for PCT/US08/57792; 4 pgs.
PCT/US2012/023277 Search Report and Written Opinion dated Apr. 5, 2012.

* cited by examiner

DEVICES AND METHODS FOR DETECTING CATHETER COMPLICATIONS

RELATED APPLICATION

This application is a Continuation-in-Part of application Ser. No. 11/731,356, filed on Mar. 30, 2007 and published on Oct. 2, 2008 as U.S. 2008/0243074.

FIELD

The present disclosure relates generally to devices, systems and methods for detecting catheter complications in implantable infusion systems.

BACKGROUND

Implantable infusions systems have been used to treat a variety of diseases, such as spasticity, pain and cancer by targeting drug delivery to a selected area of a patient. Therapies employing such systems have proven to be very helpful for patients for whom systemic therapy is not effective, possible, or practicable. The implantable systems typically include an implantable infusion device containing a reservoir for housing the drug and a catheter coupled to the reservoir to direct the drug to the target area. The devices typically include a pump or mechanism for driving fluid from the reservoir, or withdrawing fluid from the reservoir, and through the catheter to the selected area of the patient.

While perhaps the least complex component of an infusion system, catheters can have or can develop operational problems. For example, catheters may be placed in the wrong location when originally deployed, or the catheters may migrate over time such that drug-containing fluids delivered through the catheters are not delivered to the desired internal delivery site. Catheters can also become obstructed or clogged during use. A partial or complete blockage can prevent the drug-containing fluid from reaching the selected delivery site in an amount to be therapeutically effective. Catheters can also contain leaks, cuts, tears or the like, or can become dislodged from the infusion device, causing some or all of the drug-containing fluid to reach a site other than the intended delivery site.

Some infusion devices have been proposed that are capable of monitoring catheter complications, such as a leak, a dislodgement, a migration, or an occlusion. Many of these proposed infusion systems employ pressure sensors capable of monitoring pressure within the catheter to determine whether a complication or malfunction exists. Upon detection of a catheter malfunction or the likelihood of such a malfunction, the device may alert the patient to seek medical attention.

Methods and devices that use changes in physiological pressure to determine whether a catheter complication exists have recently been proposed. These methods and devices are based on the finding that physiological pressure changes can cause pressure modulations within an implanted catheter, provided that at least a portion of the catheter is placed in a fluid-filled space of the body that experiences the physiological pressures. For example, physiological pressure changes due to beating of the heart or patient breathing may be transduced through normally functioning catheters having at least a portion residing in cerebrospinal fluid (CSF). If the catheter migrates from the CSF, becomes dislodged, or develops a leak or tear at a location outside the CSF, a characteristic pressure profile associated with the physiological activity (e.g., heart beat or respiration) is not detected by a pressure sensor in communication with the catheter (and associated circuitry), and a catheter complication is determined to exist.

However, implementation of such methods in implantable infusion devices presents a number of challenges. First, development and detection of a full physiological pressure profile can require a good deal of sensing and processing power, which is not desired for an implantable infusion device with a limited power supply. However, limiting the acquisition or processing of data associated with the physiological pressure profiles may compromise the ability to detect catheter complications. Second, such physiological pressure profiles can be difficult to detect in the presence of background noise. For example, the amplitude of physiological pressure signals associated with heart beat or respiration within the CSF, and thus transmittable via a catheter positioned in the CSF, are quite small relative to pressure changes associated with patient activity. One or more of these and other challenges are addressed in one or more embodiments described herein.

SUMMARY

This disclosure, among other things, describes devices, systems and methods for detecting catheter complications via monitoring of pressure modulations within the catheter that are associated with physiological pressure changes, such as pressure changes due to heart beats. The methods, devices and systems may be configured to employ low power by limiting complexity of pressure data processed and limiting the sampling frequencies and sampling windows to those suitable for obtaining meaningful data.

The complexity of the data for processing may be reduced by preconditioning raw pressure data with a band-pass filter configured to pass through the AC component of an acquired pressure data stream that is within a relevant physiological frequency range, a rectifier and an integrator.

In some embodiments, the frequency of the pressure sampling and duration of the sampling window are determined based on population data regarding patient activity. Because patient activity may produce too much noise for meaningful pressure data to be collected, frequencies and durations of sampling may be selected based on acceptable missed detection rates, false positive rates, and latencies of detection, taking into account patient activity data as described herein. Alternatively or in addition, in some embodiments, a patient activity sensor is employed for determining whether patient activity is sufficiently low for meaningful pressure data to be collected.

In various embodiments, described herein, a method for determining status of an implanted catheter includes acquiring raw pressure data from a pressure sensor of in an implantable infusion device. The pressure sensor is in communication with a lumen of the catheter operably coupled to the infusion device. The catheter has a delivery region intended to be positioned in a fluid-filled target location of a patient. The delivery region is in communication with the lumen. The method further includes filtering the raw pressure data to remove the DC component, leaving the AC component within a relevant physiological frequency range; rectifying the AC component to produce a rectified pressure signal; obtaining a mean-magnitude of the rectified pressure signal; and determining whether the mean-magnitude is below a predetermined threshold. If the mean-magnitude is below the threshold, the catheter is determined to be in a state other than a normal state; i.e. a catheter complication exists or may exist.

Computer readable media and implantable infusion devices configured to carry out the method described above are discussed and contemplated herein.

One or more embodiments of the systems, devices and methods described herein may provide one or more advantages over prior systems, devices and methods for detecting catheter complications by sensing pressure within the catheter. Such advantages will be apparent to those of skill in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
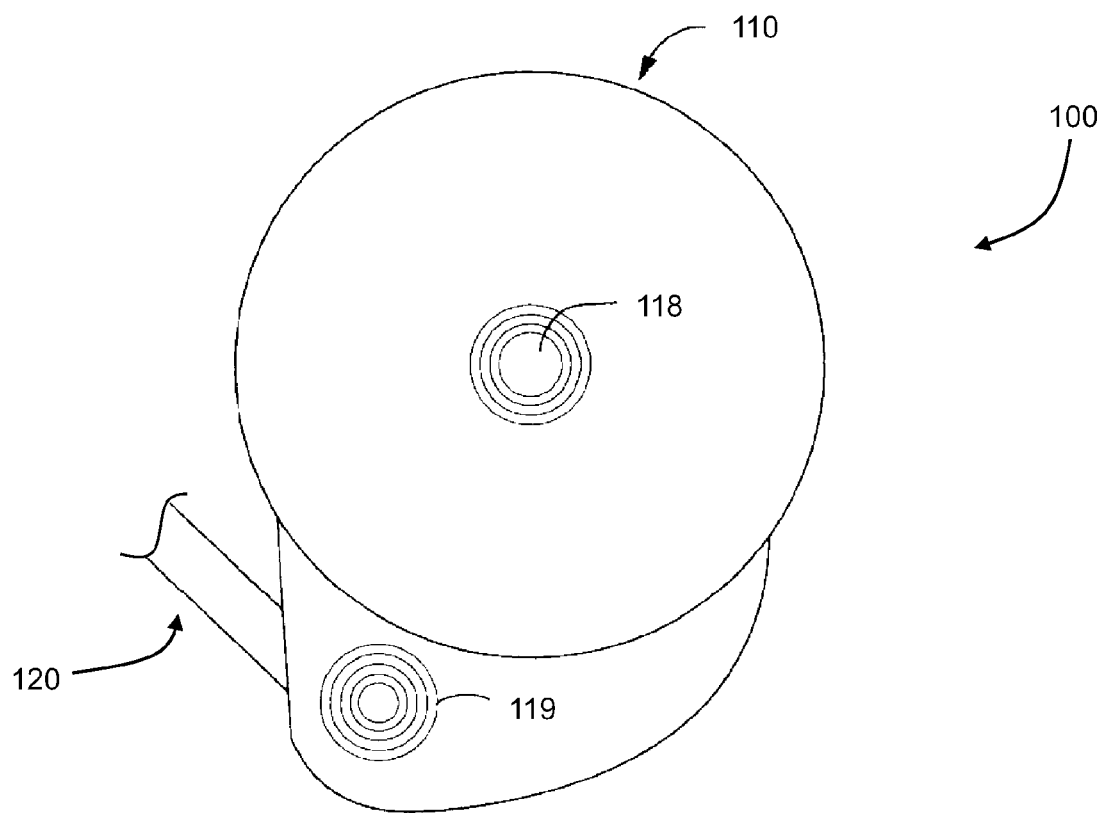
FIG. 1 is a schematic top view of an implantable infusion system that includes an implantable infusion device and a catheter.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "physiological pressure modulation profile," or the like, is a pressure profile that is modulated by a physiological event. For example, beating of a heart may result in pressure oscillations having a frequency and amplitude within characteristic ranges, which pressure oscillations are detectable in fluid-filled compartments of the patient, such in the vascular system or cerebrospinal fluid, and which may be transferred to a catheter having a delivery region or opening within the fluid-filled compartment. Such pressure oscillations have profiles that result from the physiological event (e.g., heart beat) and are examples of physiological pressure modulation profiles.

As used herein, "mean-magnitude" of a rectified (absolute value) pressure signal is the sum of the rectified values of an AC component of samples of pressure data acquired over time divided by the number of samples obtained in the period of time. The mean-magnitude may be obtained in any suitable manner. For example, the mean magnitude may be obtained by integrating the rectified pressure signal and then dividing by the number of pressure signals; the mean-magnitude may be obtained by integrating and right-shifting the rectified pressure signal, provided that the number of samples acquired is equal to 2n (2 to nth power), where n is an integer; or the like. Throughout the specification and drawings "mean magnitude" is referred to as "E" or "EU", which reflects that the mean magnitude value is related to pressure energy or energy units.

As used herein, the "AC" component of a pressure signal means the changes in pressure that reverse direction (i.e., increasing pressure then decreasing pressure) in predictable intervals and that result from physiological events, such as heart beats and breathing. The magnitude of pressure changes associated with AC component is typically small in relation to the magnitude of the baseline pressure.

As used herein, the "DC" component of a pressure signal means the magnitude of the pressure signal that is substantially constant and which is primarily determined by atmospheric pressure.

This disclosure, among other things, describes devices, systems and methods for detecting catheter complications via monitoring of pressure modulations within the catheter that are associated with physiological pressure changes, such as pressure changes due to heart beats. The methods, devices and systems may be configured to employ low power by limiting complexity of pressure data processed, limiting the sampling frequencies, or limiting the duration of sampling windows to those suitable for obtaining meaningful data.

1. Overview of Infusion Systems

Figure 2:
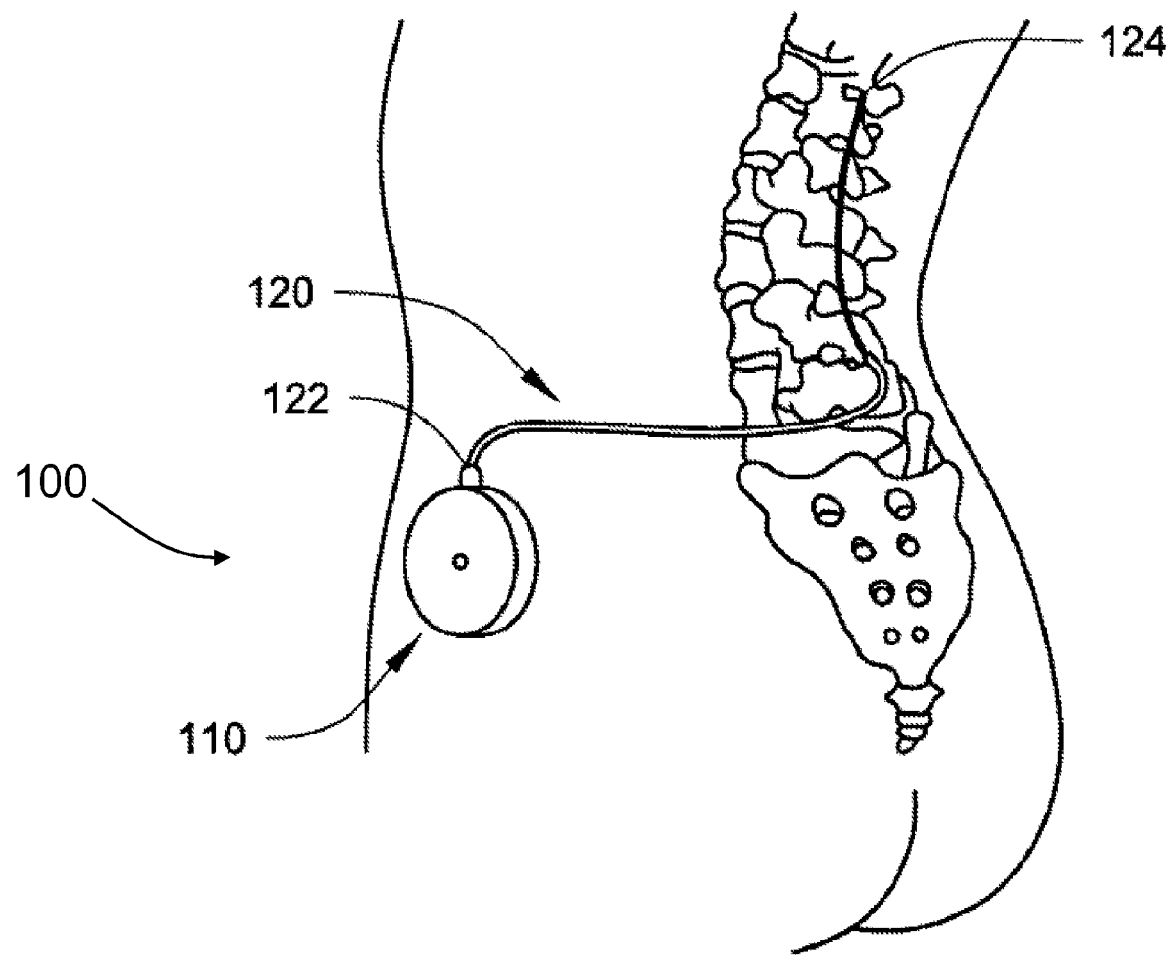
FIG. 2 is a schematic view showing an implatable infusion system implanted in a patient.

The methods and systems described herein may be employed with any suitable implantable infusion system. FIGS. 1-2 show examples of infusion systems 100 with which pressure monitoring systems and methods described herein may be used. The infusion system depicted in FIG. 1 includes an infusion device 110, a catheter 120, and a catheter access port 119 in fluid communication with the catheter 120. The infusion device 110 also includes a refill port 118 in communication with a reservoir (not shown in FIG. 1) for containing therapeutic agent disposed within the housing of the device 110. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, etc.), or the like. Examples of some potentially suitable pump assemblies may include, e.g., commercially available implantable infusion pumps such as, for example, the SYNCHROMED II and EL pumps, manufactured by Medtronic, Inc., Minneapolis, Minn.

The infusion system 100 depicted in FIG. 2 is shown implanted in a patient. The infusion system 100 includes an infusion device 110 and catheter 120 having a proximal end 122 attached to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 2, the cerebroventricles, or elsewhere as desired). While not shown in FIG. 2, it will be understood that the depicted infusion device 100 may include a catheter access port in fluid communication with the catheter 120 as described above with regard to FIG. 1. The pump assembly 110 may also include a reservoir that contains a fluid (e.g., a therapeutic substance) to be infused using the system. The fluid contained within the reservoir may preferably be replenished periodically using known techniques and structures.

Figure 3:
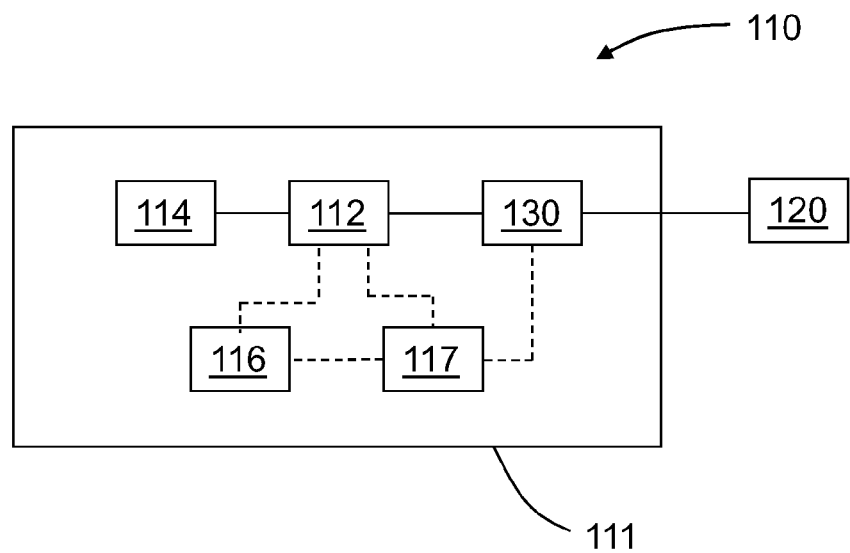
FIG. 3 is a schematic block diagram showing some selected components of an implantable infusion device, where dashed lines represent electrical connections and solid lines represent fluid connections.

An overview of selected components of an example of an implantable infusion device 110 is depicted in FIG. 3. The depicted infusion device 110 includes a pump mechanism 112 operably coupled to a catheter 120 such that fluid within a reservoir 114 can be delivered to the catheter 120 via the pump mechanism 112. The depicted infusion device 110 includes a power supply 116 and control electronics 117 operably coupled to the power supply 116 and the pump mechanism 112 such that the infusion of fluids using the system can be controlled. Although not specifically depicted, the infusion device 110 may also include other components such as, e.g., communication devices (e.g., telemetry modules, etc.) to provide for control and/or communication between the infusion system and external devices.

The implantable infusion device 110 depicted in FIG. 3 also includes a pressure sensor 130 that is operably coupled to the control electronics 117. The pressure sensor 130 is operably coupled to the catheter 120 in a manner that allows the pressure sensor 130 to measure the pressure of fluid located within the catheter 120 and to provide a pressure signal (to, e.g., the control electronics 117) that is representative of the fluid pressure of the fluid in the catheter 120.

Figure 4:
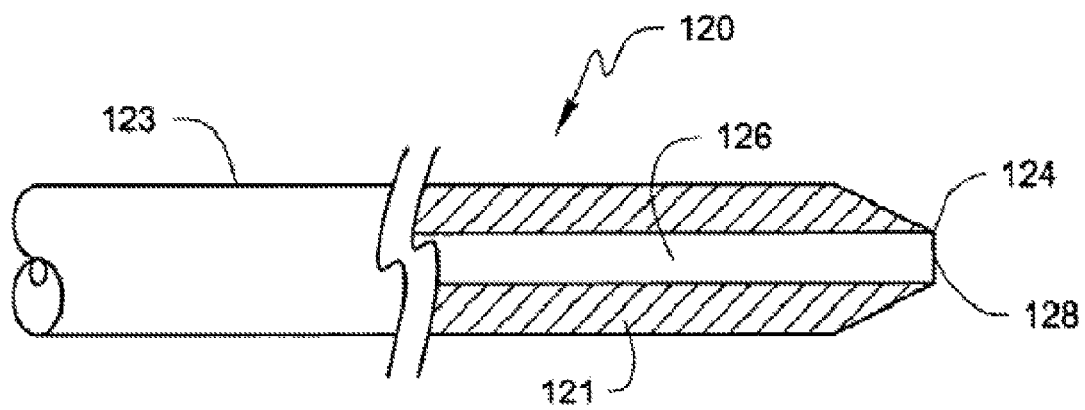
FIG. 4 is a partial sectional view of a portion of a catheter.

FIG. 4 depicts a portion of a catheter 120 in an enlarged cross-sectional view. The catheter 120 includes an elongated tubular portion 123 that preferably extends from the proximal end (not shown) to the distal end 124. The catheter 120 depicted in FIG. 4 includes a lumen 126 that terminates at opening 128 (or delivery region) at the distal end 124. Therapeutic substances (or other fluids) delivered from the infusion device 110 to the catheter 120 pass through lumen 126 and preferably exit the catheter 120 through opening 128 (also referred to herein as "delivery region" or "infusion section").

The body of catheter 120 may be constructed of any suitable material, e.g., an elastomeric tube. Examples of some suitable materials include, but are not limited to, silicone rubber (e.g., polydimethyl siloxane) or polyurethane, both of which can provide good mechanical properties and are very flexible. Suitable materials for the catheter 120 are also preferably chemically inert such that they will not interact with therapeutic substances, body tissues, or body fluids while implanted in the patient.

Where the catheter is to be used for intrathecal fluid delivery, it may be preferred that at least a portion of the catheter 120 be sized to fit in the gap between the spinal cord and the dura within the intrathecal space. Catheters intended for delivering fluids to other internal delivery sites will be sized appropriately for those locations. As another consideration in sizing the catheter, the diameter of the lumen 126 is preferably large enough to accommodate expected infusion rates with acceptable flow resistance. The wall 121 of the catheter 120 is preferably thick enough to withstand normal handling during the implant procedure and forces from body tissues during normal motion. As an example, a catheter intended for use in intrathecal fluid delivery may have an outside diameter of 1.25 millimeters (mm), an inside diameter of 0.5 mm, and a wall thickness of 0.375 mm. Such a catheter may have a length of, e.g., 50 centimeters (cm) long to reach from, e.g., a drug infusion pump implanted in the patient's abdomen to the spine.

Although the opening 128 through which the fluid exits the catheter 120 is depicted as a single opening in the distal end 124 of catheter 120, such an opening 128 is only one embodiment of an infusion section that may be used in connection with the teachings presented herein. Other embodiments of infusion sections may include, e.g., multiple openings, permeable membranes, or the like. Although the infusion section (opening 128) of the depicted catheter 120 is located at the distal end 124 of the catheter 120, the infusion section(s) may be positioned at any location along the length of the catheter 120 that can be used to deliver the fluid to the selected internal delivery site.

2. Physiological Pressure Modulations

Because physiological pressure modulations at the selected internal delivery site are preferably transmitted into the fluid located within the lumens of catheters in various embodiments, the construction of the infusion sections is preferably selected to provide for that pressure transmission. In other words, the infusion sections are preferably capable of transmitting physiological pressure modulations (e.g., from the CSF where the infusion sections may be located) into the fluid located within the catheter lumen.

As mentioned above, one way to determine the status of a catheter of an implantable infusion device is to monitor pressure within a lumen of a catheter for characteristic physiologic pressure changes of cerebral spinal fluid (CSF) in which the catheter is implanted. Examples of such methods are described in U.S. Patent Application Publication No. 2008/0243074A1, entitled CATHETER MALFUNCTION DETERMINATIONS USING PHYSIOLOGIC PRESSURE, published on Oct. 2, 2008, which publication is incorporated herein by reference in its entirety to the extent that it does not conflict with the disclosure presented herein.

Figure 5:
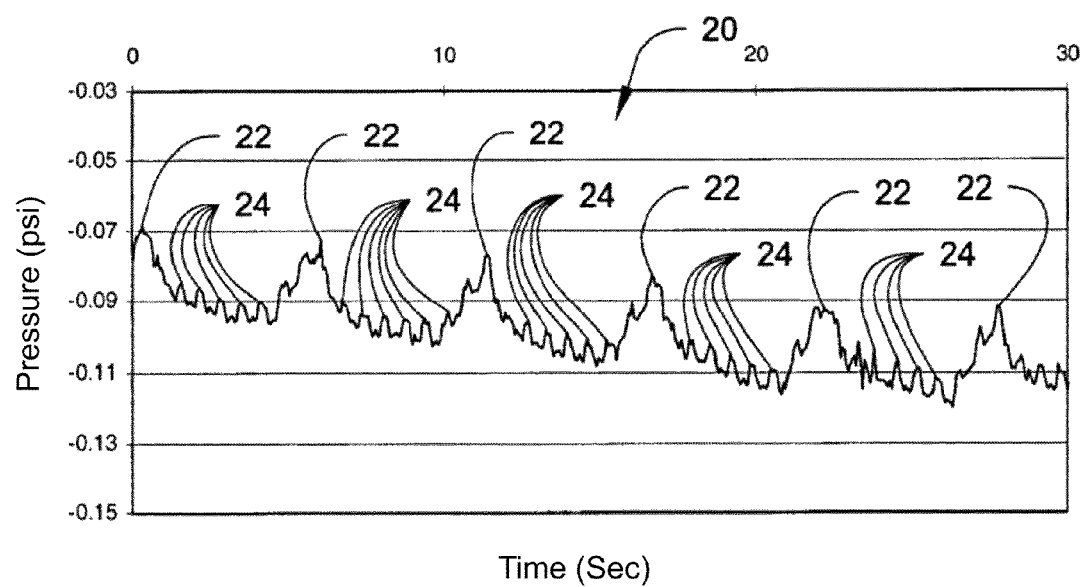
FIG. 5 is a graph of pressure versus time within a catheter located in the CSF in the intrathecal space of a subject.

An example of a representative pressure profile of CSF in an animal, such as a sheep or dog, on mechanical ventilation is shown in FIG. 5. Pressure in the CSF has characteristic patterns that can be transmitted to a catheter in communication with the CSF. The representative data plotted in FIG. 5 demonstrates these patterns, where the plot 20 represents pressure of fluid within a lumen of a catheter located in fluid communication with the CSF. The pressure profile includes repeating major peaks 22 representative of patient respiration activity and repeating minor peaks 24 representative of cardiac activity (i.e., heartbeats). The major peaks 22 and minor peaks 24 are transmitted into the fluid in the lumen from the CSF (into which the lumen opens). The major peaks 22 repeat about every 2 to 10 seconds, which corresponds to about 30 to 6 breaths per minute. Typically, major peaks 22 repeat about every 3 to 5 seconds, which corresponds to about 20 to 12 breaths per minute. The amplitude of the major peaks 22 can vary (e.g., depending on the nature of the catheter), but are often less than 4 mmHg in amplitude, typically between about 1 mmHg and about 4 mmHg or between about 1 mmHg and 3 mmHg within a catheter such as Medtronic, Inc.'s Model 8709SC or 8731SC silicone catheters with an inner diameter of about 0.53 mm.

The minor peaks 24 repeat about every half second to about every second and a half, which corresponds to about 40 to 120 heart beats per minute. Typically, the minor peaks 24 repeat about every 0.6 seconds to about every 1 second, corresponding to a heart rate of about 100 beats per minute to about 60 beats per minute. The amplitude of the minor peaks 24 can vary (e.g., depending on the nature of the catheter), but are often between about 0.5 mmHg and about 1 mmHg in amplitude within a catheter such as Medtronic, Inc.'s Model 8709SC or 8731SC silicone catheters with an inner diameter of about 0.53 mm.

It should be noted that the pressure associated with respiration (major peaks 22) is exaggerated in cases where an animal is on mechanical ventilation (e.g, as shown in FIG. 5) relative to a free-breathing animal. Accordingly, the differences in amplitude of the peaks corresponding to respiration (major peaks) and heart rate (minor peaks) may not be as discernable in a free-breathing animal or human. It will be understood pressure changes that generally repeat in coordination with the animal's or patient's breathing or heart rate may be detected, regardless of the amplitude. In some instances, it may be difficult to detect pressure changes associated with both breathing and heart rate. However, pressure changes in the CSF or other fluid filled compartment associated with one or the other of heart rate and respiration are typically detectable and are transmittable via a catheter having an infusion section opening into the compartment. In some embodiments, characteristic pressure changes associated with one or both of heart rate and respiration are detected to determine catheter status.

Figure 6:
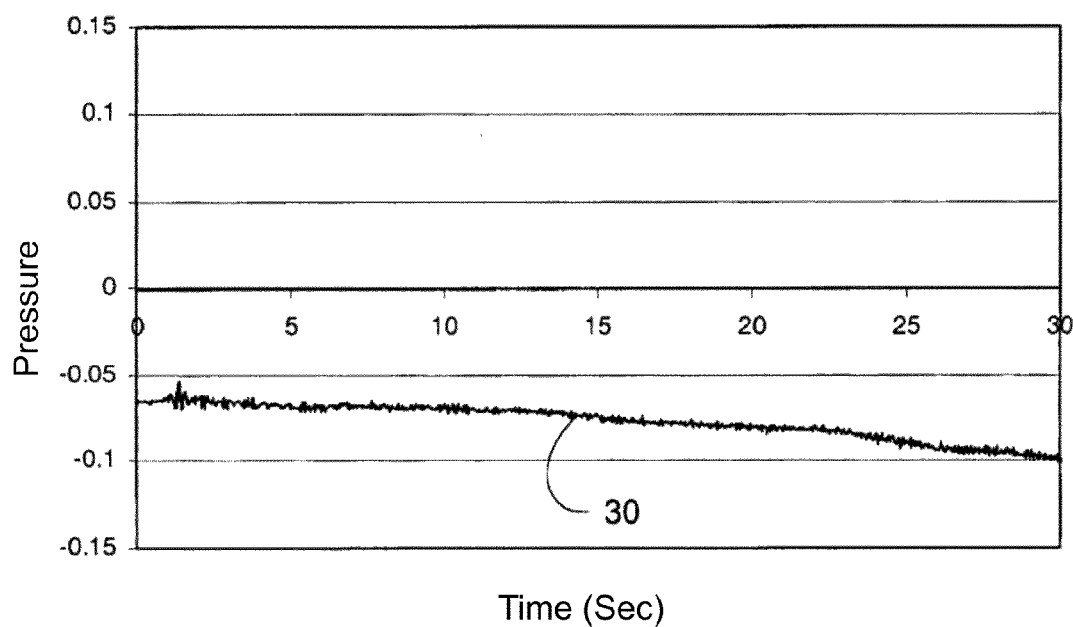
FIG. 6 is a graph of pressure versus time within a catheter located outside of the CSF a subject.

Referring now to FIG. 6, a representative physiological pressure profile of a catheter having a delivery region located outside the CSF in a non-fluid compartment of an animal is shown. As depicted in FIG. 6, representative physiological pressures are not detected within catheters located in non-fluid filled compartments as the physiological signal is attenuated. Similar attenuation is expected with a variety of other catheter states, as indicated below in Table 1.

TABLE 1

Expected attenuation values for a variety of catheter states

| Catheter State | Expected Attenuation (at 1 Hz) |
|---|---|
| Normal | 0 dB |
| Partial occlusion (10X increased restriction) | −12 dB |
| Migration from intrathecal to epidural | −12 dB |
| Full occlusion (100X increased restriction) | −30 dB |
| Disconnect | −40 dB |
| Air bubble (¼ length of catheter) | −14 dB |

It should be understood that the values presented above may vary with the nature of the catheter and infusion device employed. However, regardless of the catheter and infusion device employed, the attenuation associated with a catheter complication should result in sufficient loss of signal for a determination that a catheter complication exists when employing embodiments of the methods described herein.

It should also be understood that the ability to detect a catheter complication via the ability (or lack of ability) to detect a characteristic physiological pressure modulation profile can be affected by noise. For purposes of example, noise will be described with regard to the AC signal related to a patient's cardiac and respiratory pressure as measured via a catheter in communication with a patient's CSF. In this context, noise has two types: patient CSF noise and sensor sampling system noise. The CSF noise arises from pressure signals within the relevant frequency range (e.g., 0.5 to 3 Hz) due to patient movement or posture change (collectively referred to herein as "patient activity"). Sensor and sampling system noise provides a minimal signal amplitude that needs to be obtained for purposes of meaningful data collection. Through filtering or other pre-processing of raw pressure data, sensor and sampling system noise can readily be reduced to manageable levels. However, CSF noise can render it nearly impossible to detect a catheter complication during periods of patient activity.

For example, assuming that relevant physiological pressure (e.g. cardiac or respiratory) amplitudes range from 1 to 5 mmHg from peak to peak, patient activity (due to, e.g., walking) that falls within the relevant frequency range can result in signals of greater than 10 mmHg, such as around 20 mmHg. Accordingly in various embodiments (described in more detail below), pressure data is sampled at a high enough frequency to increase the chances that, during at least some sampling windows, meaningful pressure data is obtained. However, a balance should be reached between sampling frequency (and sampling window duration) and the power requirements of such sampling and data processing, as higher frequency sampling typically requires more power.

3. Data Processing and Complication Detection

Various embodiments are described herein that provide a practical approach for detecting physiological pressure modulations for purposes of determining whether a catheter complication exists in an implanted infusion system. One or more of these embodiments balance the power concerns of an implantable infusion system, which have a limited power supply (e.g., battery) or require recharging or replenishing (e.g., rechargeable battery) of the power supply, with the need to obtain and process sufficient data to make reliable determinations as to catheter status.

Figure 7:
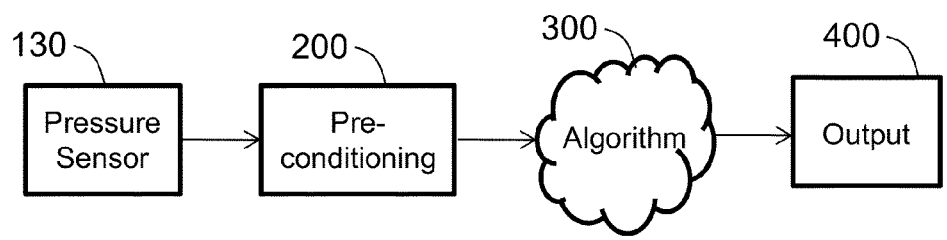
FIG. 7 is a schematic drawing of an over view of data processing and components in accordance with various embodiments described herein.

In general, the methods, devices and systems described herein process pressure data as indicated in FIG. 7. Where raw pressure data (input pressure data or "$P_{in}$") obtained from pressure sensor 130 is pre-conditioned by components 200 before algorithm processing by components 300 for determining whether a catheter complication exists. Components 300 may include a processor, memory (such as RAM, ROM, or the like), or the like. The memory may store computer-readable instructions that enable the processor to carry out an algorithm as described herein. An appropriate output, such as alerting a patient or physician or storing results in memory, may be made by components 400.

Figure 8:
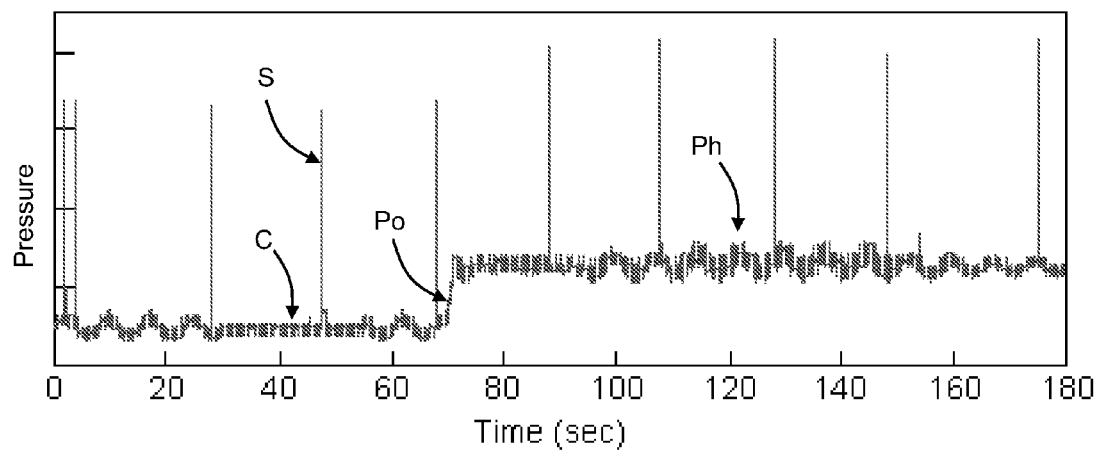
FIG. 8 is a simulated graph of pressure versus time of a catheter located outside of the CSF a subject.

For purposes of illustration, graphical depictions of results of various steps of processing of data, according to some embodiments, will be shown. The raw pressure data that is used as the input for purposes of illustration is shown in the simulated plot in FIG. 8, which includes the DC pressure level, cardiac and respiratory physiological AC pressure signals (Ph) and occasional pulse due to a pump stroke (S) (of a piston pump). For purposes of illustration, catheter complications (C) between about 30 and 55 seconds and between about 70 and 95 seconds, and a change in pressure (Po) due to a posture change from a patient standing up from a supine position (assuming catheter location in lumbar intrathecal space) is shown. The simulated plot depicted in FIG. 8, is based on previous studies showing, with the particular system employed, the amplitude of CSF artifacts that track with the patient's cardiac and respiratory rhythms are roughly between 1 mmHg and 5 mmHg peak to peak with frequencies between 2 Hz down to ¹⁄₁₀ Hz depending on patient activity levels. For example, at-rest cardiac base frequency can be between 30 bps for an extreme athlete to 120 bps for a patient exhibiting tachycardia.

A. Pre-Conditioning

In various embodiments described herein, raw pressure data is preconditioned to reduce the complexity of the data for processing, thereby reducing the power requirements for processing the data. As discussed above (e.g., with regard to Table 1) catheter complications result in a diminishing of the characteristic physiological cardiac and respiratory artifacts ordinarily present in the CSF as read by a pressure sensor in communication with the lumen of a catheter having an infusion section placed in a patient's CSF. Therefore, a technical approach for a complication detection algorithm described in accordance with various embodiments presented herein is to merely measure an "energy" level in a particular band of physiologic interest.

This unitless energy level may be derived from a root mean square average of a sampled data stream in any suitable manner. By way of example and with reference to FIG. 9, raw analog pressure data obtained from pressure sensor 130 may be preprocessed by components 200, which include an analog-to-digital converter 210, a band pass filter 220, a rectifier 230, and an integrator 240. Preferably the band pass filter 220 is configured to remove the average DC pressure component and to pass only the time-varying portion of the pressure signal through. In addition, the band pass filter 220 is preferably configured to filter out noise that is above the frequency band of interest. In various embodiments, the band pass filter with a lower frequency cutoff of between 0.1 and 1 Hz and with an upper frequency cutoff of between 2 Hz and 5Hz. In some embodiments, the band pass filter has a lower frequency cutoff between 0.1 Hz and 0.5, such as between 0.2 and 0.5 Hz, and has an upper frequency cutoff of between 2 and 4 Hz, such as between 2 and 3 Hz.

It will be understood that the low frequency component of the band pass filter will typically determine the filter settling time (i.e., the amount of time to achieve a reliable baseline measurement). For example, a 0.1 Hz band-pass filter may require approximately 10 to 20 seconds to settle out. For implantable medical devices that have limited battery life, such long settling times may be unacceptable. For example, the amount of time of a sampling window can be considered to be the sum of (i) data acquisition on time, (ii) filter settling time, and (iii) algorithm dwell time (time needed to gather enough data for meaningful processing). The data acquisition turn on time is relatively short—typically less than a second. If cardiac or respiratory CSF physiological pressure signals are used for determining catheter complications, a minimum dwell time of about 5 to 15 seconds may be need to include a reasonable number of heart beats or respiratory cycles. Accordingly, if the filter settling time is between 10 and 20 seconds, it can account for more than 50% of the total data acquisition energy consumed. However, a 0.5 Hz band-pass filter typically requires 5× less time to settle out than a 0.1 Hz filter. The use of a 0.5 Hz filter will thus result in much more efficient data acquisition, but may result in the loss of the frequencies needed to detect patient respirations.

Figure 10:
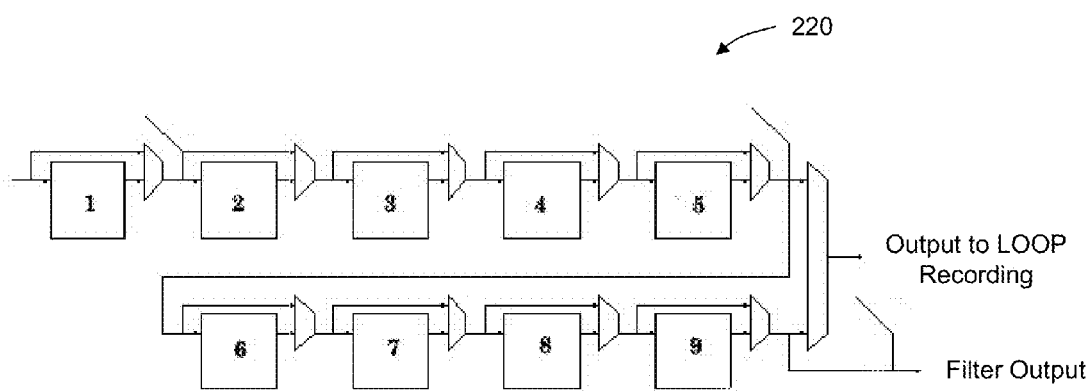
FIG. 10 is a schematic block diagram of an embodiment of a band-pass filter.

In some embodiments, the band-pass filter 220 includes a chain of two or more stages of $2^{nd}$ order bi-quad filters as shown in FIG. 10. In the depicted filter 220, a band-pass is implemented by cascading two biquad stages. The first stage is configured as a High Pass biquad and the flowing stage is configured as a Low Pass biquad.

The band-pass filter requirements are preferably selected to optimize the signal-to-noise-ratio (SNR) between cardiac physiological pressure and sensor noise over the range of possible frequencies of use. The pressure signal from CSF is a superimposition of the cardiac base frequency and a third harmonic of the base frequency. It is assumed that the detection system will support at-rest heart rates between 30 and 120 bps. The corresponding frequency range for this is 0.5 Hz to 2 Hz. The computed physiological energy (discussed below in more detail) will include components of base frequency and the $3^{rd}$ harmonic. As the high-frequency cutoff of the band pass filter moves down, the contribution from the $3^{rd}$ harmonic decreases. However, the total sensor noise component will likewise decrease as described below in Equation 1.

Sensor to noise ratio   Equation 1

$$SNR = \frac{CardiacEnergy}{SensorNoiseEnergy}$$

Figure 11:
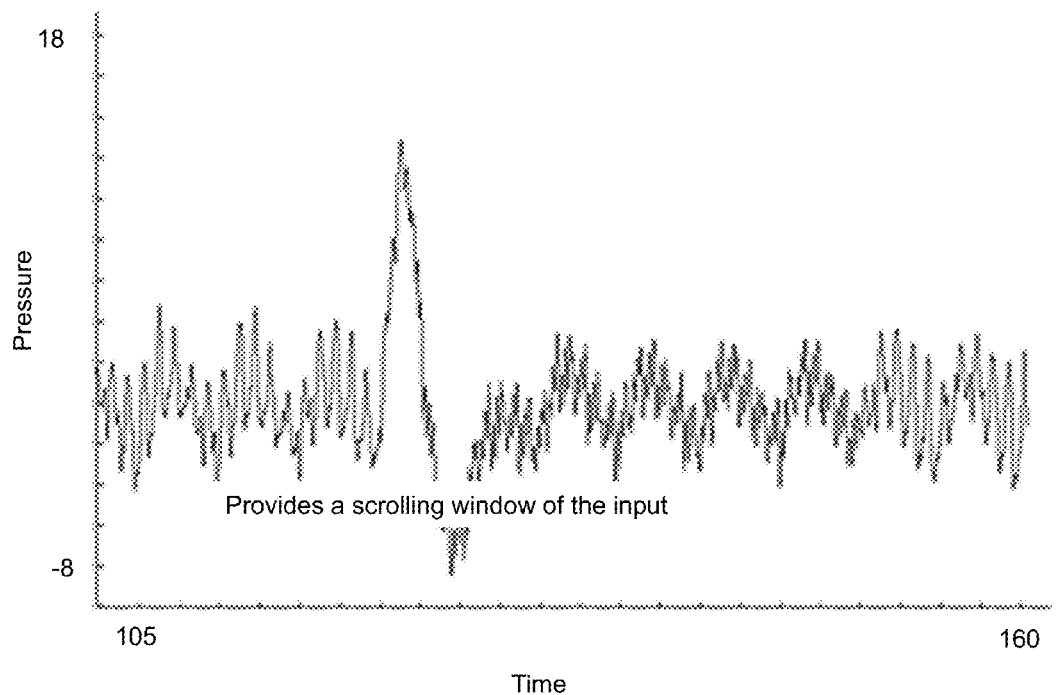
FIG. 11 is a simulated graph of pressure versus time of the pressure data depicted in FIG. 8 following band-pass filtering.

A simulated plot of the resulting pressure data after passing the band pass filter (0.1-3 Hz) 220 is shown in FIG. 11.

Figure 9:
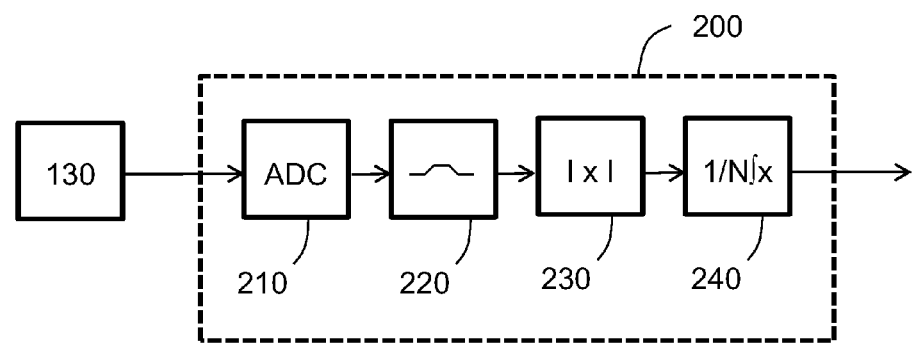
FIG. 9 is a schematic block diagram showing selected preconditioning components and processing according to various embodiments described herein.

The pressure signal resulting from band pass filter 220 is then rectified by rectifier 230 and integrated by integrator 240 (see, e.g., FIG. 9). The rectifier 230 may take the absolute values of data samples of the pressure signal resulting from the band pass filter or may square the values of the data samples. The integrator 240 also serves a low-pass filter. In various embodiments, the block 240 integrates, dumps, and right shifts the pressure data received from the rectifier block 230 to compute the average for a set of samples collected over the sampling window. It will be understood that data obtained during the settling time of the band-pass filter 220 may not be meaningful and should be accounted for by the integrator 240. For example, in some embodiments, only data acquired later in the sampling period is integrated.

Figure 12:
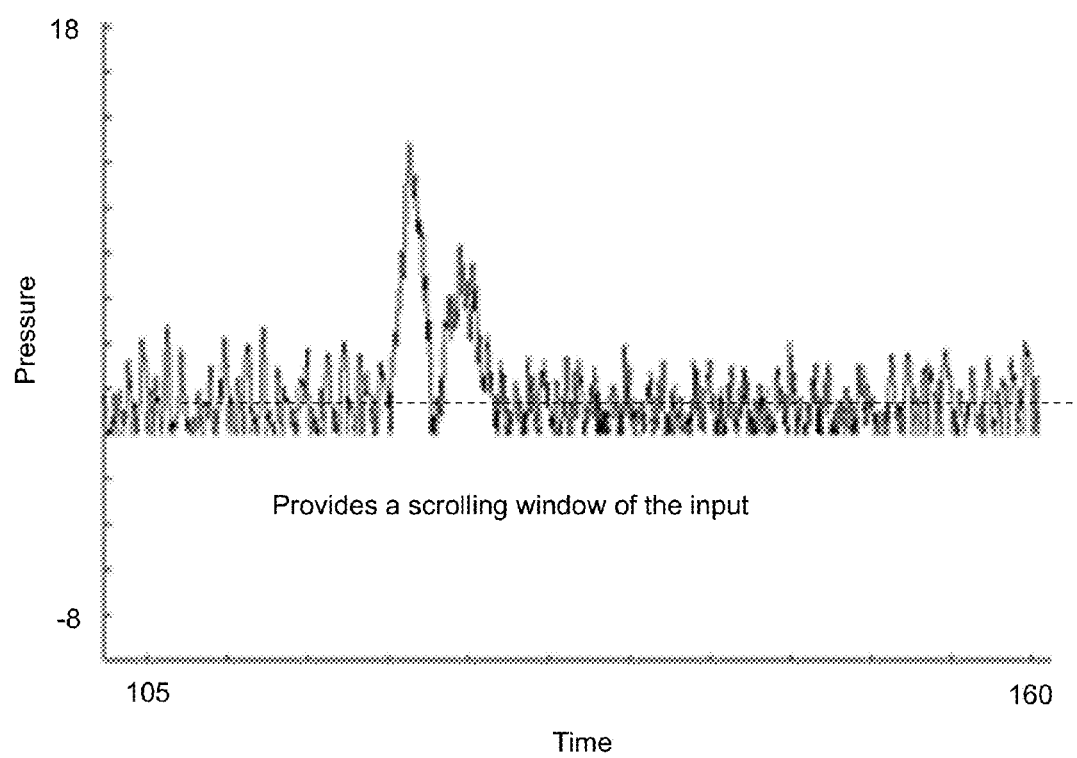
FIG. 12 is a simulated graph of pressure versus time of the pressure data depicted in FIG. 8 following band-pass filtering and rectifying.

A simulated plot of the data received from block 220 after passing through blocks 230 and 240 is shown in FIG. 12, where the dashed line shows the computed average for the sampling window.

The output of the preconditioning sub-blocks 210, 220, 230, 240 is a value corresponding to the amount of CSF signal magnitude in the cardiac and respiratory frequencies measured by a pressure sensor in communication with a lumen of a catheter in communication with the CSF. The effect of applying the preconditioning sub-blocks of band pass-filter 220, rectifier 230, integrate, divide and dump 240 is to create mean-magnitude average (MM) of the sampled data stream. A mathematical conversion is:

$MM$ conversion from sampled data stream   Equation 2

$$p_{MM} = \frac{1}{N}\sum_{i=1}^{N}|p_i|$$

It will be understood that the mean-magnitude is similar to a root-mean square (RMS) average. That is, if the rectifier squared the sampled values (e.g., if rectifier were a diode), then the square root could be taken of the sum of the squared sampled values divided by the number of sampled values to obtain the RMS average. For purposes of the present disclosure, RMS is subsumed under the definition of "mean-magnitude."

If the sampled data is a well-behaved sinusoid, the conversion from a peak-to-peak magnitude will be:

Peak-Peak to $MM$ conversion (ideal sign wave)   Equation 3

$$p_{MM} = \frac{\sqrt{2}}{4}p_{pp}$$

In various embodiments, a measure of mean magnitude (EU) is calculated from $P_{MM}$ for signals having peak-to-peak spectral signal amplitudes ($A_f$) as follows:

Mean magnitude ($EU$) calculation   Equation 4

$$EU = \frac{\sqrt{2}\cdot A_f}{4}\sum_{f=1}^{N}A_f$$

A mean magnitude calculation of a CSF cardiac signal having a fundamental frequency and a third harmonic component may be made as follows:

Mean magnitude ($EU$) calculation of signal having $3^{rd}$   Equation 5
harmonic component $$EU = \frac{\sqrt{2}\cdot T_{duration}}{4}\cdot(A_1 H(f_1) + A_3\cdot H(3\cdot f_1))$$

Figure 13:
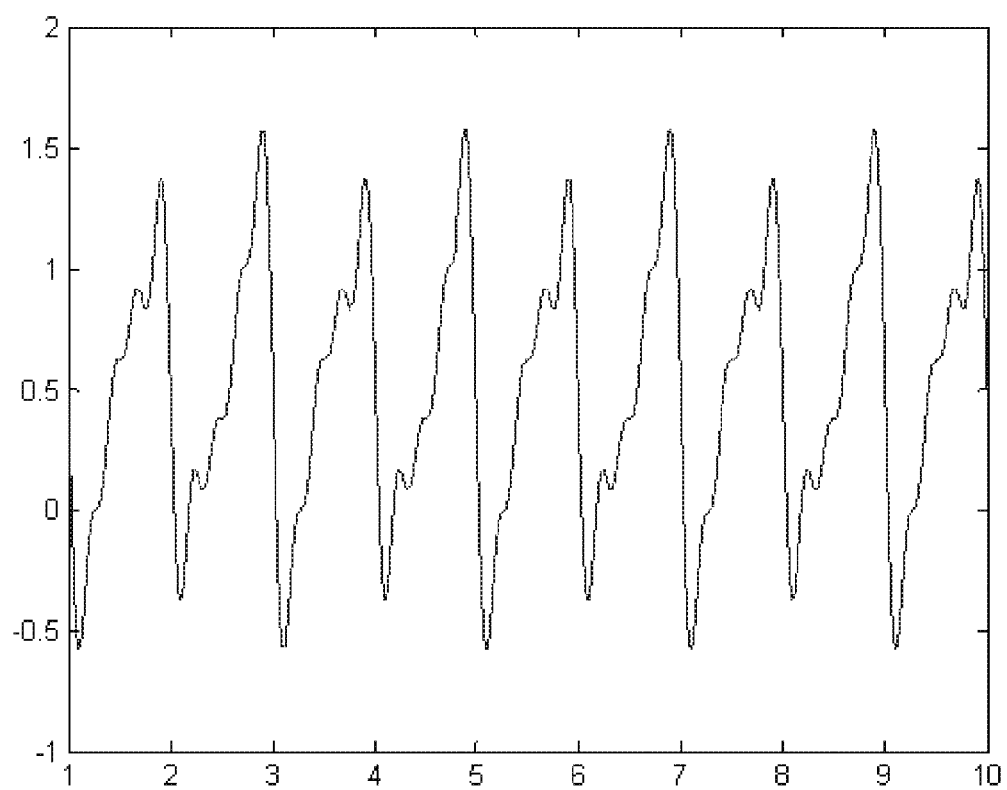
FIG. 13 is a simulated plot of pressure versus time showing a CSF pressure cardiac effect artifact.

Based on typical CSF signal waveforms captured using direct pressure measurement, the relative amplitude of the first and third harmonic are approximately ⅓ as shown in FIG. 13.

A respiratory frequency component (about ⅙ the heart rate) also contributes to the CSF signal that will pass through the digital band-pass filter, H(f), if the low frequency component of the band-pass filter is at a sufficiently low frequency (e.g. 0.1 Hz). The resultant energy value can be predicted to be a function of cardiac signal frequency and amplitude and will be affected by the filter transfer function, H(f).

Mean magnitude ($EU$) calculation accounting for filter   Equation 6
transfer function and cardiac and respiratory components $$EU(f_c, A_c, A_r) = \frac{\sqrt{2}\cdot T_{duration}}{4}\cdot\left(A_c\cdot H(f_c) + \frac{A_c}{3}\cdot H(3\cdot f_c) + A_r\cdot H\left(\frac{f_c}{6}\right)\right)$$

The transfer function, for CSF inputs to the sensor, is actually a composite of the band-pass filter and the effective filtering action provided by the catheter itself. The catheter behaves as a simple $1^{st}$ order low pass filter with attenuation equal to:

Catheter attenuation   Equation 7

$$H_{cath}(f, fc) = \frac{f_c}{f + f_c}$$

B. Catheter Complication Algorithm

Any suitable algorithm for determining whether the mean magnitude derived from pre-conditioning components 200, as described above, may be used to determine whether a catheter complication exists. As discussed above, a variety of catheter complications will result in attenuation and diminished mean magnitude associated with CSF pressure modulation profiles. Thus, if the mean magnitude is below a predetermined minimum, a determination may be made that a catheter complication exists or may exist.

Figure 14:
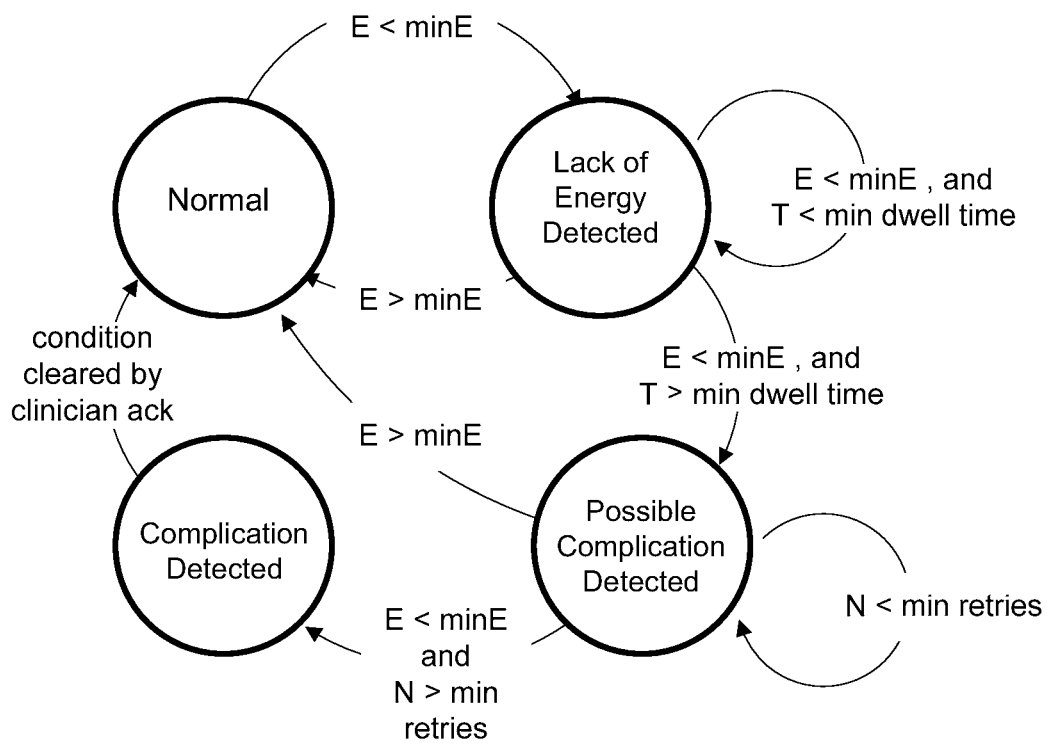
FIG. 14 is a schematic depiction of a Markov state machine model in accordance with various embodiments described herein.

In various embodiments, the algorithm (block 300 see, e.g., FIG. 7) includes a Markov model state machine that translates mean magnitude (E) to discrete catheter states. As depicted in FIG. 14, the Markov state machine includes at least two discrete catheter states "Normal" and "Complication Detected." The state machine may include additional discrete catheter states, such as "Lack of Energy Detected" and "Possible Complication Detected" to reduce false detection rates, if necessary or desired.

Figure 15:
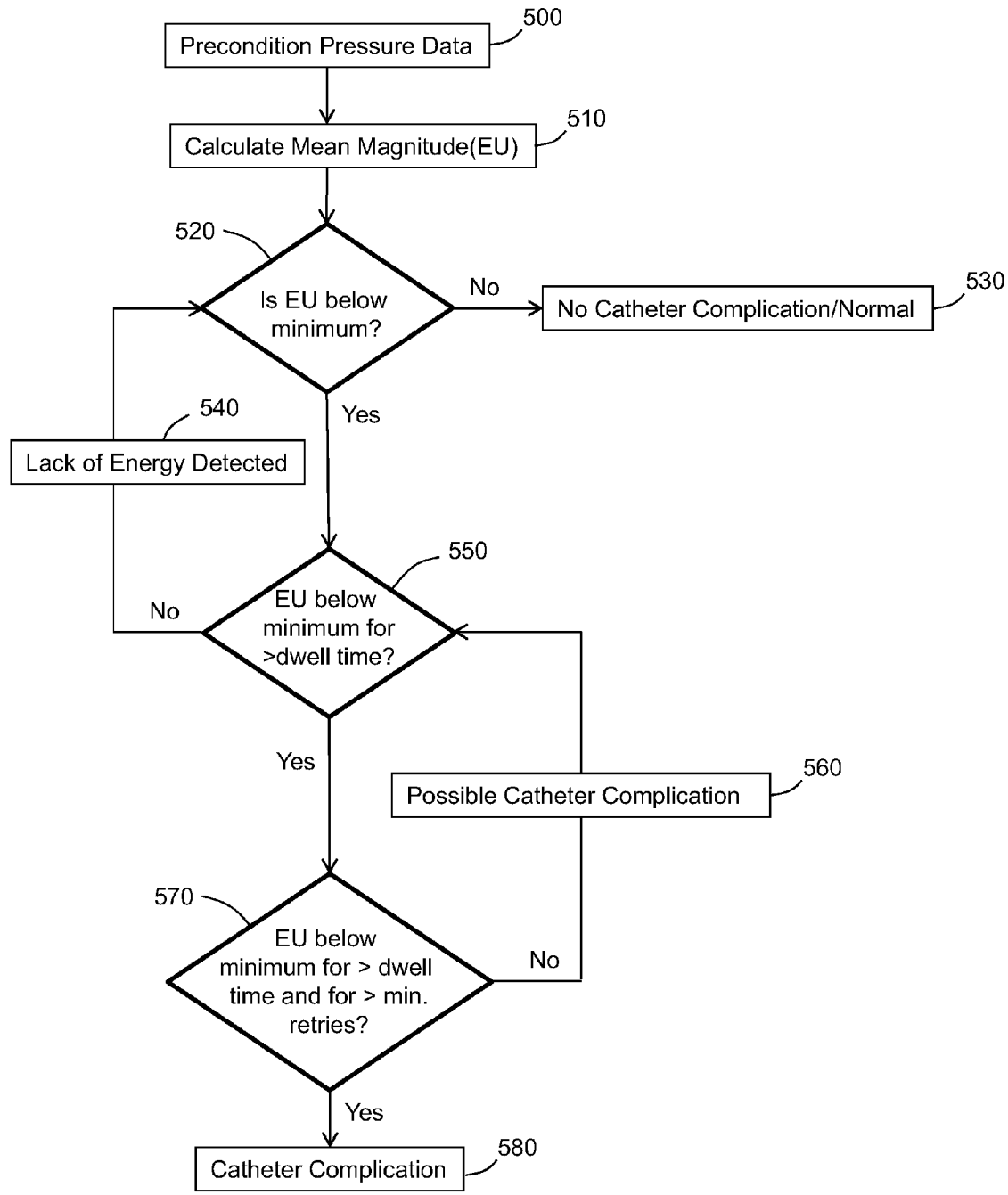
FIG. 15 is a flow diagram of an overview of a method described herein.

An overview of the process employed with regard to the Markov state machine depicted in FIG. 14 is shown in the flow diagram of FIG. 15. As shown in FIG. 15, raw pressure data is preconditioned (500), e.g. as described above. An mean magnitude (EU) is derived from the preconditioned pressure data (510), e.g. as described above. A determination is then made as to whether the EU is below a predetermined minimum (520). The predetermined minimum may be determined by balancing the desire to minimize "missed detection" of known occurrences and "false detection" of complications for properly functioning catheters (e.g. as described in more detail below under the heading "Detection Threshold Analysis"). If the EU is not below the minimum, the catheter is in the "Normal" state and catheter complication is determined not to exist (530). If the EU is below the predetermined minimum, a determination as to whether the EU is below the minimum for a time greater than a minimum dwell time may then be made (550). If the EU is not below the energy minimum for a time greater than a minimum dwell time, a "lack of energy" state is observed (540). If the EU is below the minimum for a time greater than a minimum dwell time, a determination as to whether the EU is below the energy minimum for a time greater than a minimum dwell time and for greater than a predetermined minimum number or retries may then be made (570). If the EU is not below the energy minimum for a time greater than a minimum dwell time and for greater than a predetermined minimum number or retries, a "possible catheter complication" state is observed (560). If the EU is below the energy minimum for a time greater than a minimum dwell time and for greater than a predetermined minimum number or retries, a "catheter complication" state is observed (580).

i. Accounting for Gain/Sensor Variation/Sensitivity

Figure 16:
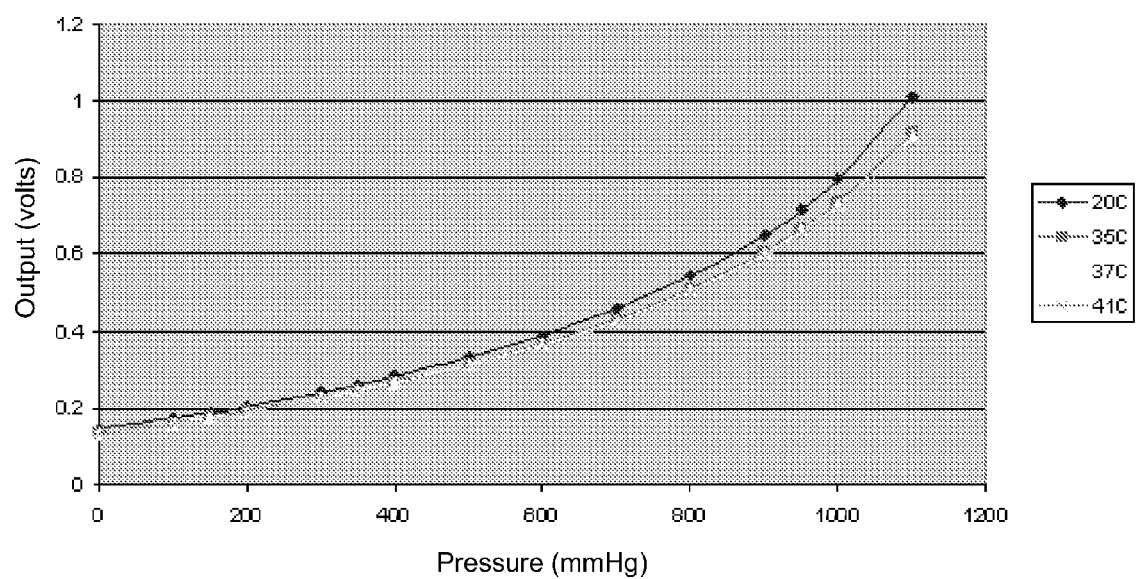
FIG. 16 is simulated plot of voltage versus pressure relationship for a sensor at various temperatures.

As discussed below with regard to FIGS. 16-18, it may be desirable to apply an appropriate correction factor to integrated pressure data or mean magnitude to account for sensor gain or variation because sensor output and conversion is not necessarily linear.

In various embodiments, pressure sensor data is converted into digital numeric format in a set of two transforms. In the first transform, the sensor converts pressure into voltage via a functional relationship as shown in FIG. 16, which shows that the pressure to voltage transformation provided by the sensor is not necessarily a linear one. Over the expected operating range of pressures (400 mmHg to 800 mmHg), the sensitivity (or, gain) of the filter can change (e.g., from a value of 0.4 mV/mmHg to 0.8 mV/mmHg as shown in the embodiment depicted in FIG. 17). (Sensor Sensitivity is defined by $$S = \frac{\Delta V}{\Delta P}$$

such that the sensor output, in volts, is given by $V_S = S \cdot P +$ Offset). In FIG. 17, the target sensitivity of 0.0008 V/mmHg is depicted by closed circles, the upper sensitivity limit is depicted by vertical dash marks, and the lower sensitivity limit is depicted by asterisks.

Figure 17:
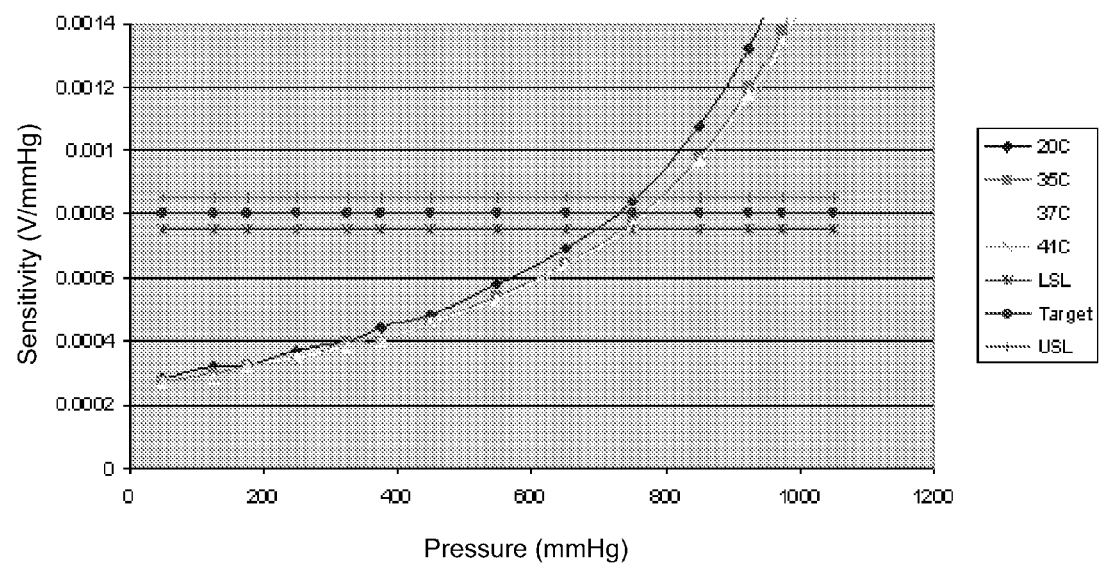
FIG. 17 is a plot of simulated pressure sensor sensitivity as a function of pressure.

As shown in the embodiment depicted in FIG. 17, absent correction, computed mean magnitude (EU) could be over (or under) by an amount proportional to the deviation from the presumed sensor sensitivity. For example, a sensor with a presumed sensitivity of 0.8 that is operating at 400 mmHg, which has an actual sensitivity of 0.4, could lead to an undercalculation of EU by 50%. On the other hand, operation at low temperature at 800 mmHg could lead to an over-calculation of EU by 15%.

Accordingly, it may be desirable to correct for such sensor gain. This can be done by calibrating the sensor prior to use by collecting a number of values within the relevant pressure ranges (e.g., 400 mmHg to 800 mmHg) and identifying a correction factor curve or compensation coefficient for application to detected raw pressures during actual use. The calibration curve or correction factors can stored in a lookup table.

Figure 18:
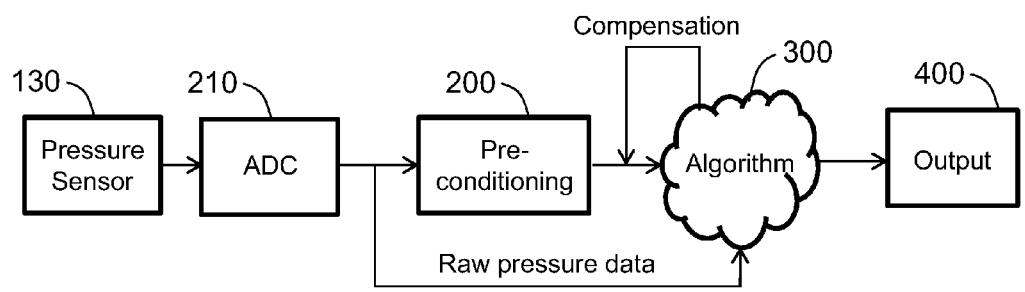
FIG. 18 is a schematic drawing of an overview of data processing and components in accordance with various embodiments described herein.

By way of example and with reference to FIG. 18, raw pressure data (e.g., following ADC, but before band pass filtering) not subjected to preconditioning 200 may obtained for purposes of identifying a pressure point for applying the appropriate compensation factor to account for sensor gain.

C. Sampling Frequency and Window Duration

Any suitable sampling frequency and sampling window duration may be employed in accordance with the teachings presented herein. Preferably, the sampling frequency and window duration take into account desired performance characteristics in light of power consumption issues. Three key performance measures of the catheter complication algorithm described herein are (i) missed detection rate, (ii) false detection rate, and (iii) latency of detection.

Missed detection rate is the probability that the algorithm will not detect a catheter complication within the specified worst case latency period when an actual catheter complication does exist. Any suitable missed detection rate may be employed. However, as the missed detection rate approaches zero, increased sampling (and power consumption) is needed. Missed detection rate is a unitless quantity. In various embodiments, the missed detection rate is set between about 3% and about 10%, such as about 5% or about 6%.

False detection rate is the probability that algorithm and device will detect a catheter complication when no problem actual exists. This is a unit-less quantity. Any suitable missed detection rate may be employed. However, as the set missed detection rate approaches zero, increased sampling (and power consumption) is needed. False detection rate is a unitless quantity. In various embodiments, the false detection rate is set between about 0% and about 5%.

Latency of detection is the amount of time from onset before the algorithm will detect a catheter complication condition. Both average and worst case measures of latency can be important. Units of detection latency are used herein are hours. Any suitable average and worst case latency of detection may be employed. However, the shorter the set latency, the more sampling (and power consumption) required.

Testing to identify suitable missed detection rates, false detection rates, and latencies of detection was performed in two parts. The first part provided an understanding of the mean magnitude pressure values and ranges for expected and worst case conditions of CSF pressure signals and catheter states which were used to support prediction of missed and false detection rates. The second part provided an understanding of latency. This testing incorporated a stochastic model of patient activity which was then monitored relative to varying sampling frequencies and durations.

i. Detection Threshold Analysis

For the system employed herein, raw intrathecal CSF pressure signals have a range of 1.2-3.9 mmHg peak-to-peak due to patient variations. Each catheter state also presents a range of attenuation values based on the frequency of the cardiac rate. The greatest attenuation (−1.7 dB) will occur at the highest cardiac rate (2 Hz) and the least attenuation (−0.14 dB) will occur at the lowest cardiac rate (0.5 Hz). The superposition of the range of CSF pressure signal magnitudes and the attenuations at the lower and upper end of the heart rate resulted in the calculation of a set of four values (quadruple). The quadruple was calculated for each of 7 catheter complication states, and the results are presented below in Table 2.

TABLE 2

Simulated Physiological Mean Magnitude (MM) Pressure Values for a variety of patient and catheter states

| Condition | MM value for 1.20 pp min at 2 Hz in mmHg | MM value for 1.20 pp min at .5 Hz in mmHg | MM value for 3.9 pp max at 2 Hz in mmHg | MM value for 3.9 pp max at .5 Hz in mmHg |
|---|---|---|---|---|
| Normal 8709SC, normal patient (−1.7 dB to −.14 dB) | 0.288 | 0.413 | 1.122 | 1.342 |
| 10X Increased Restriction (−9 to −12 dB) | 0.072 | 0.104 | 0.398 | 0.476 |
| Migration - epi (−9 to −12 dB) | 0.072 | 0.104 | 0.398 | 0.476 |
| 100X Occlusion (−20 to −30 dB) | 0.009 | 0.013 | 0.112 | 0.134 |
| Migration - full (−20 to −30 dB) | 0.009 | 0.013 | 0.112 | 0.134 |
| Disconnect (−35 to −40 dB) | 0.003 | 0.004 | 0.020 | 0.069 |
| Air bubble - 50 uL bubble (−5 to −14 dB) | 0.057 | 0.082 | 0.631 | 0.755 |

Figure 19:
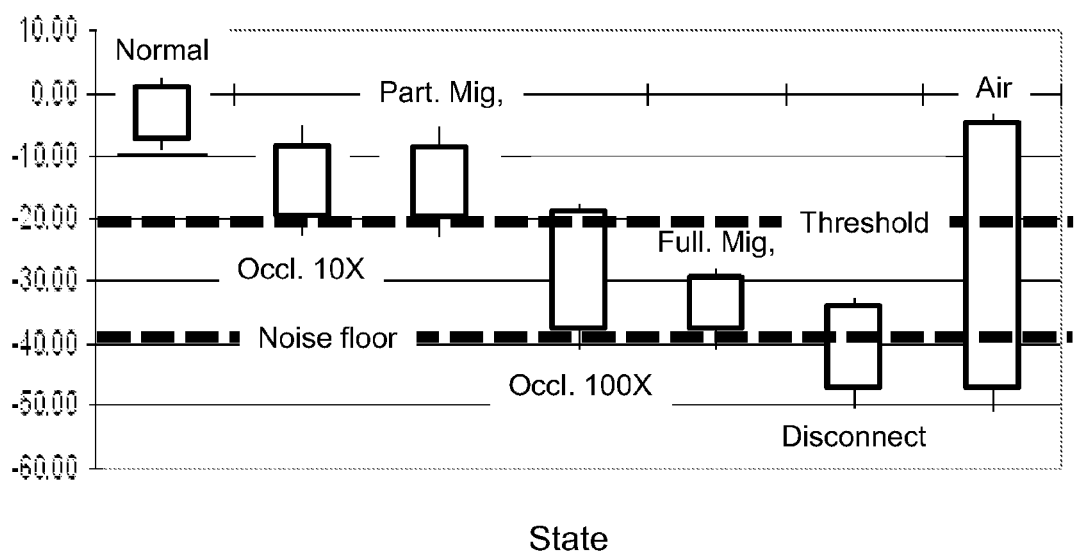
FIG. 19 is a simulated plot of energy levels during periods of patient activity.

These computed mean magnitude values are shown graphically in FIG. 19. For reference, the infusion device's pressure measurement, post-filtered, noise floor (−40 dB) as well as the selected complication threshold, are overlaid in FIG. 19. For the 0 dB reference, a 2.86 mmHg pk-pk (or, 1 mmHg MM) signal is assumed.

In the tested system, an occlusion does not present any measurable degradation in flow accuracy until it reaches approximately 100× (100 times the occlusion or resistance to flow of a normal length patent catheter). The "10× Occlusion" state may not be considered a must-detect complication, as a sufficient amount of fluid will likely be able to be delivered though such a catheter. For similar reasons, a "Partial Migration" may not be considered a must-detect complication since the infusion section of the catheter remains in communication with CSF, and hence, drug delivery to the CSF continues.

Selection of the proper detection threshold is a tradeoff between minimizing "Missed Detection" of known complications occurrences and "False Detection" of complications for properly functioning catheters.

For the example presented in FIG. 19, a threshold of −20 dB may be a suitable reference level or 1 mmHg RMS. This corresponds to a value of 0.1 mmHg MM in the tested system. This selection provides 9 dB of margin between the minimal signal level for a normal and patent catheter. This margin is important to minimize False Detection of complications. Gain shift or gain uncertainty of the pressure sensor also adds to the range of each of the expected MM values for each catheter state, which can be compensated for as described above.

With regard to "Missed Detections," a −20 dB threshold slightly overlaps the expected distribution of "100× Occlusion" signal levels. However, with this threshold, it is expected that about 84% of catheter occlusions will be detected. Further, as catheter occlusions account for about 30% of the overall catheter complications that are typically detected, an overall catheter complication detection rate with this threshold in this system is expected to be about 95%. Thus, the missed detection rate should be about 5%.

ii. Latency Analysis

Results of the present simulation testing indicate that patient activities will tend to mask the ability to detect catheter complications. For example, simple walking results in 0.67 g's of peak-to-peak acceleration. This translates into 20 mmHg peak-to peak which is four times the magnitude of a large cardiac pressure signal.

During periods of patient activity, even with catheter complication states, large MM values of pressure, that are above any practical detection threshold, are predicted. Complications will rarely be detectable during periods of patient activity. Hence, in various embodiments described herein, the algorithm relies on the assumption that patients do not always exhibit high levels of activity (at least as it relates to measured catheter pressure). In various embodiments, the algorithm (or device executing the algorithm) will sample data for a window of time at regularly spaced intervals. The duration and periodicity of these sampling windows may be determined by analysis of human motion activity profiles, as described below.

Figure 20:
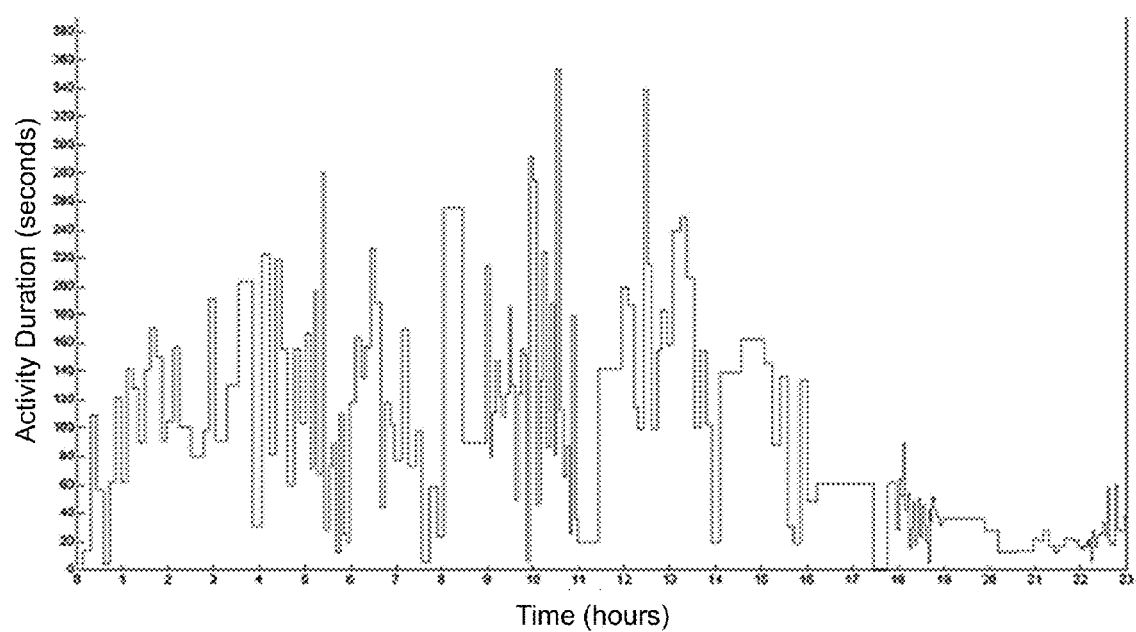
FIG. 20 is a plot of activity duration per hour versus hour of day.

In the simulation discussed below, actual patient activity data from a population of patients was used to augment the CSF pressure model with realistic activity patterns. The data was used to generate a stochastic profile of daily activity characterized total duration of activity episodes per hour versus hour of the day as shown in FIG. 20.

Figure 21:
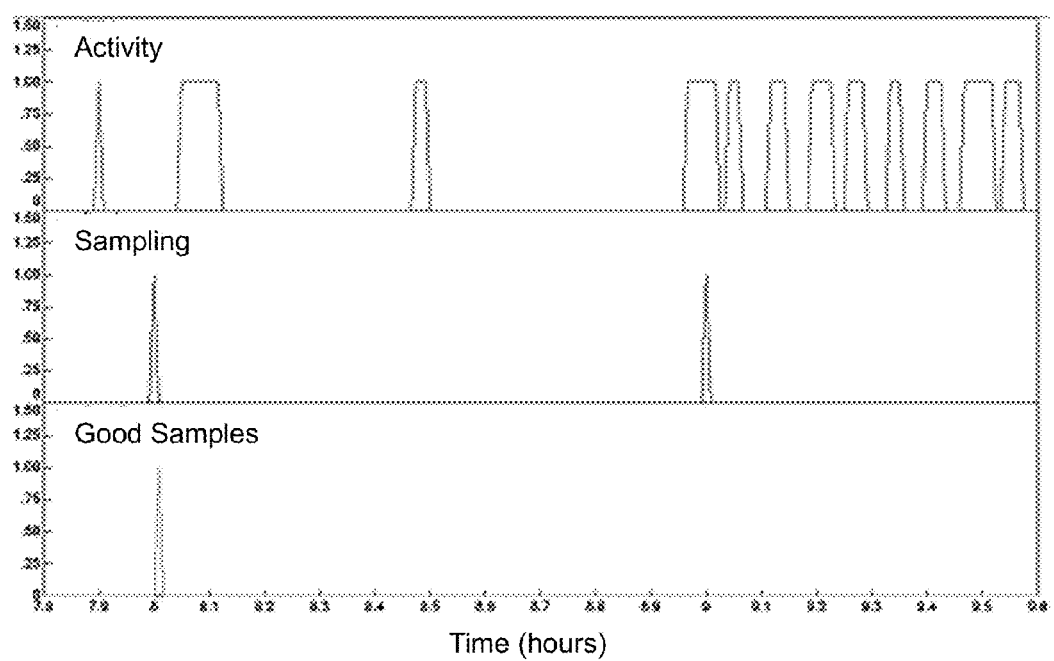
FIG. 21 is a zoomed in view of a simulation record of activity and sampling windows.
Figure 22:
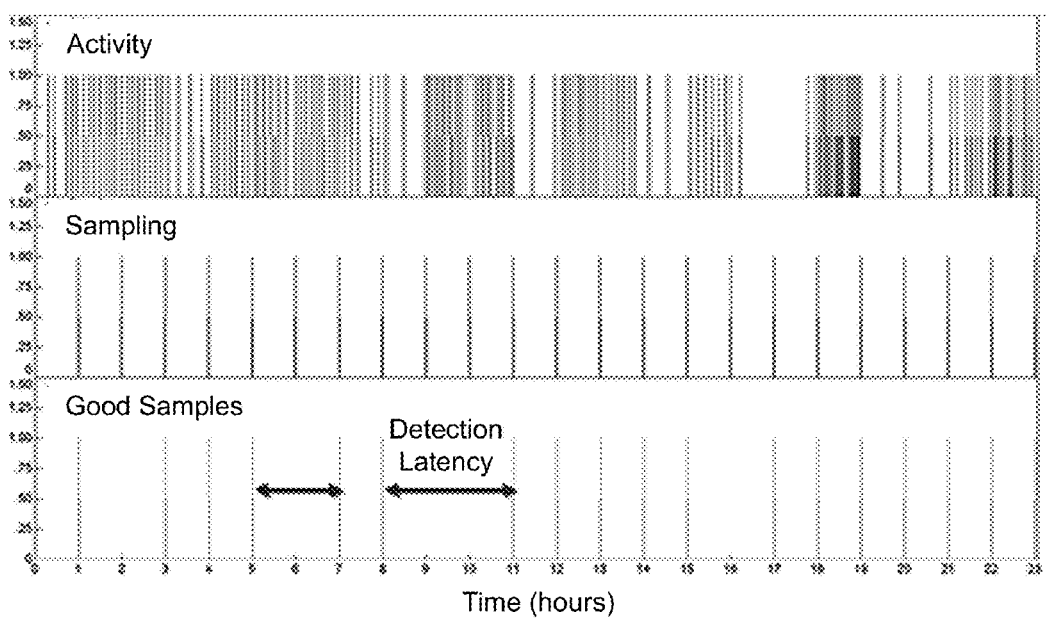
FIG. 22 is a full 24 hour view of a simulation record of activity and sampling windows.

Algorithm simulation was used to determine the number of sampling windows that occurred during periods of non-activity (good or quiet periods) relative to the total number of sampling windows. FIG. 21 and FIG. 22 show a two hour and the full 24-hours of simulation trace. In FIGS. 21-22, the top panel reflects activity, the middle panel represents sampling, and the bottom panel represents samples obtained during a time of patient inactivity.

Figure 23:
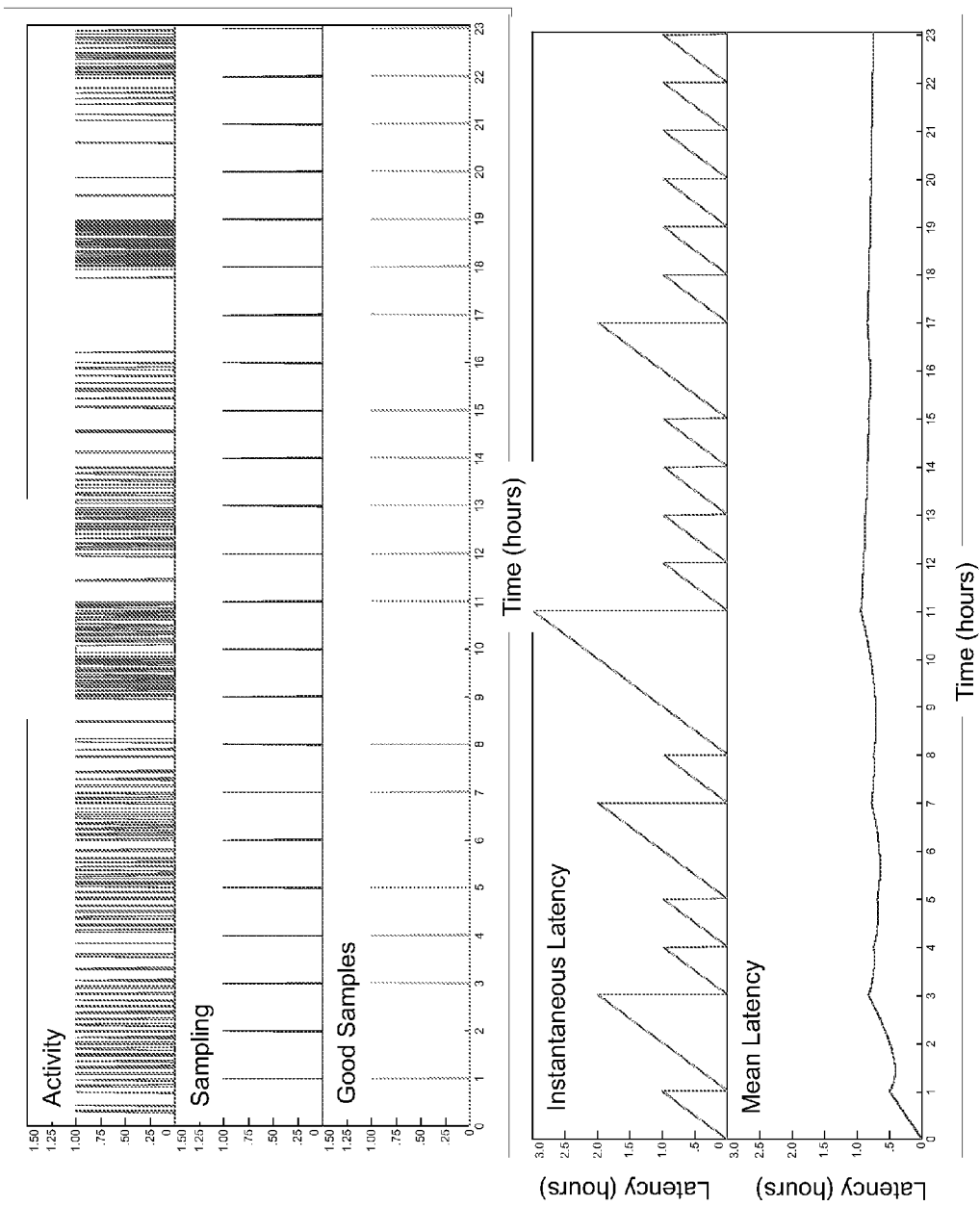
FIG. 23 is a plot of activity simulation with latency calculation included.

The sampling window durations and the sampling frequency were varied each yielding different simulation output traces. In addition, instantaneous and average latency calculations were added to the simulation as shown in FIG. 23. Sampling window durations were varied from 5 seconds to 240 seconds. In addition, the frequency of sampling was varied from 3 per day (once every 8 hours) to 96 per day (4 per hour).

Figure 24:
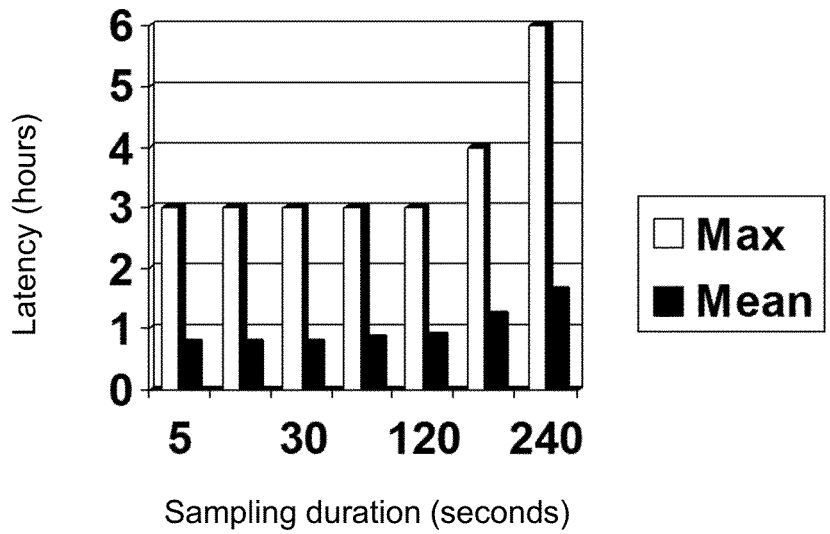
FIG. 24 is a bar graph of maximum and mean latency for varying sizes of sampling window durations (based on 1 sampling per hour).
Figure 25:
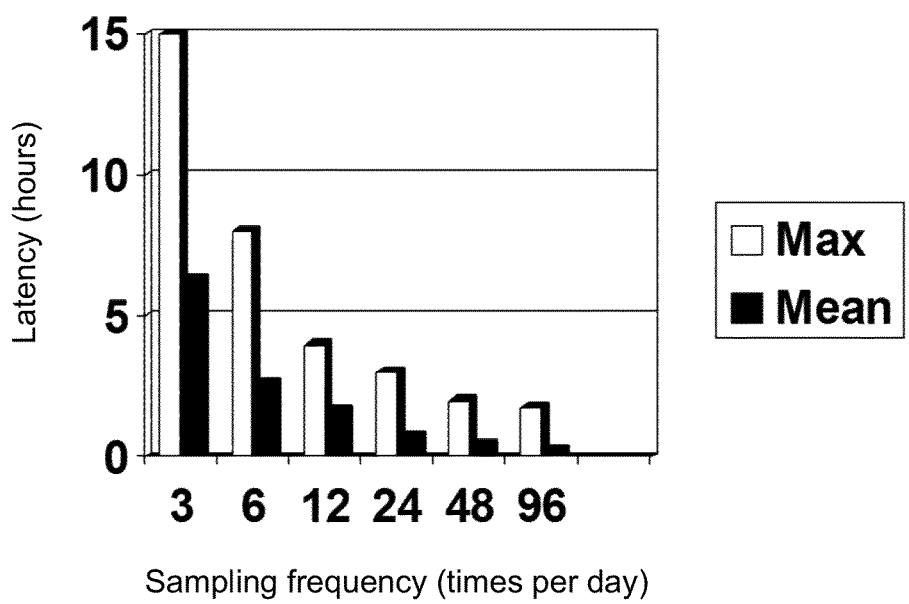
FIG. 25 is a bar graph of maximum and mean expected latency for varying sampling frequencies (samples per day) assuming a 15 second window duration.

FIG. 24 presents the maximum and mean expected latency for varying sizes of sampling window durations (based on one sampling per hour). FIG. 25 presents the maximum and mean expected latency for varying sizes of sampling frequencies (based on a 15 second window duration).

As shown in FIG. 24, a sample duration of as little of 5 seconds should provide suitable latencies of detection. However, the sample duration should be sufficiently long to obtain meaningful data from a reasonable number of cardiac or respiratory physiological cycles. Accordingly, a 10 to 20 second window may be desirable. Of course, filter settling time may also need to be accounted for, e.g. as discussed above. In some embodiments, a 30 second window is used to account for filter settling time, yet still obtain data from a reasonable number of physiological cycles. As depicted in FIG. 24, a 30 second sampling window duration should provide reasonable mean and maximum latencies.

As shown in FIG. 25, sampling at about once an hour (or 24 times in a day) should provide similar mean and maximum latencies to those obtainable with 15-30 second window durations.

Of course, any suitable or desired sampling window duration or frequency of sampling may be selected by using the results presented herein or obtainable using methods described herein.

Figure 26:
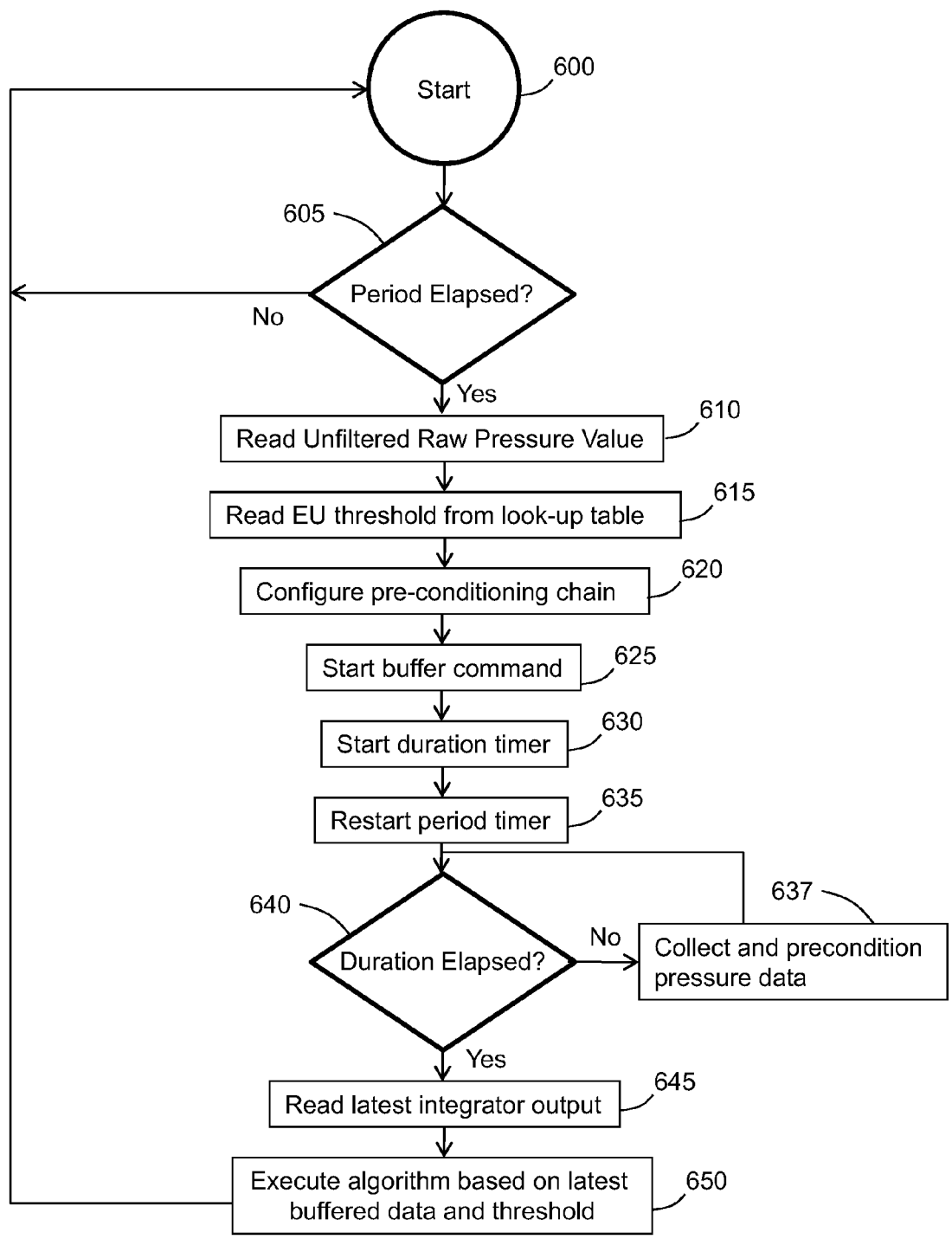
FIG. 26 is a flow diagram of an overview of a method in accordance with various embodiments described herein.

Referring now to FIG. 26, an example of an embodiment of a method carried out by an implantable infusion device for determining the state of a catheter in accordance with the teachings presented herein is shown. As a particular detection cycle starts (600) a determination is made as to whether the time period since the last detection cycle has elapsed (605). If the time period has not elapsed, detection is delayed. If the period has elapsed, raw unfiltered processing data is read (610) and an energy unit correction factor for the raw data is identified from a lookup table (615) based on sensor calibration. The preconditioning chain is configured (620) and a buffer command is started (625). The duration (sampling window duration) timer is started (630) and the period (sampling frequency period) timer is restarted (635). Until the sample window duration has been determined to have elapsed (640), pressure data is collected and preconditioned (637). Once the sample window duration has been determined to have elapsed (640), pressure data is no longer collected. The latest integrator output is read (645) and the algorithm for determining catheter status is executed based on the latest buffered data and threshold (650).

Of course, this is only one suitable way for a process described herein to be carried out. It will be understood that additional processes may be used for carrying out the methods described herein.

D. Activity Sensor

As an alternative or in addition to selecting suitable sampling frequencies and sample window durations to ensure that meaningful data can be captured during a period of patient activity, one or more activity sensors may be employed in accordance with the methods and systems described herein. The activity sensors may be used to determine that a patient is sufficiently inactive for meaningful pressure data to be collected.

Any suitable activity sensor may be employed. For example, activity sensors and configurations described in US 2005/0234518, entitled "Collecting Activity and Sleep Quality Information via a Medical Device", published on Oct. 20, 2005, filed on Mar. 16, 2005, naming Kenneth T. Heruth and Keith A. Miesel as inventors (which is incorporated herein by reference in its entirety to the extent that it does not conflict with the disclosure presented herein), may be used or modified for use with the methods and systems described herein. Examples of sensors that may be used to detect patient activity are accelerometers, heart rate detectors or ECGs, muscle tone monitors, and the like. The activity sensors may be implanted or may be external and in communication with the implanted device.

Figure 27:
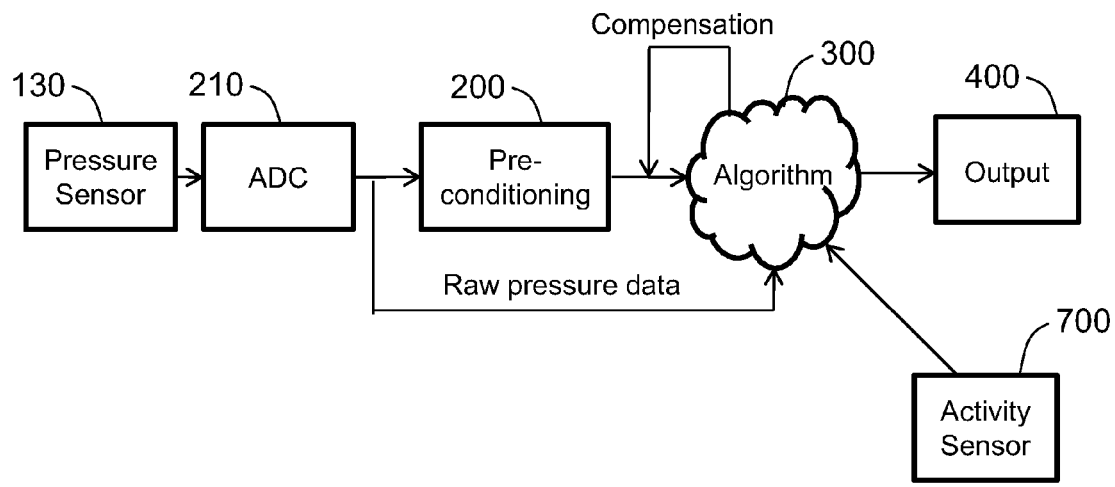
FIG. 27 is a schematic drawing of an overview of data processing and components in accordance with various embodiments described herein.

Referring now to FIG. 27, an overview of a method for determining catheter status via pressure sensing in conjunction with activity sensing is described. The method depicted in FIG. 27 is similar to that depicted in, and described above with regard to, FIG. 18 with like reference numbers referring to like or similar steps and components. As shown in FIG. 27, the systems and methods described herein may include one or more activity sensors or incorporate information from the activity sensors in determining whether a catheter complication exists. When data received from the activity sensor (and associated electronics, such as an analog-to-digital converter or the like) is indicative of sufficiently low activity such that meaningful physiological pressure modulation profiles may be obtained, the pressure readings may be acquired and processed as described above.

Figure 28:
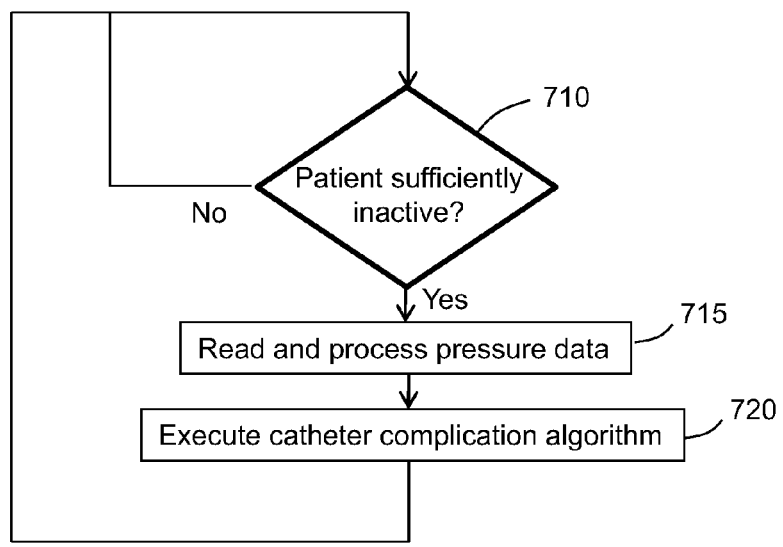
FIG. 28 is a flow diagram of an overview of a method in accordance with various embodiments described herein.

Referring now to FIG. 28, a flow diagram of a method employing activity sensing is depicted. In the depicted method, a determination is made as to whether the patient is sufficiently inactive to obtain meaningful pressure data based on data from the activity sensor (710). If the patient is determined to be sufficiently inactive, pressure data is acquired and processed (715), e.g. as described above, and a catheter complication algorithm is executed (720), e.g. as described above. While not shown, it may be desirable to include period and duration timers with the method shown in FIG. 28.

4. Output

Figure 29:
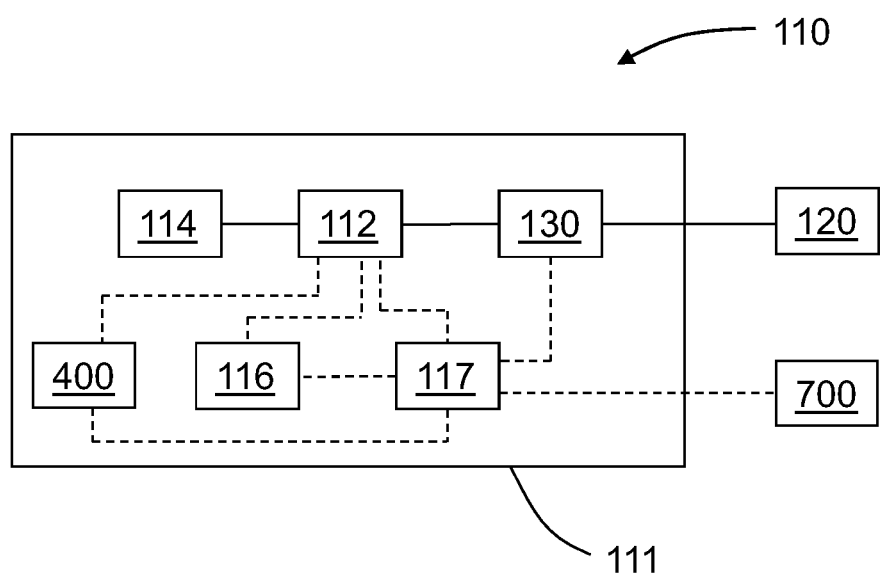
FIG. 29 is a schematic block diagram showing selected components of an implantable infusion device.

If a catheter complication or a catheter state other than "Normal" is detected, the implantable infusion device may have one or more output components to alert the patient or a healthcare provider of the potential catheter complication, to record the event, or the like. For example and with reference to FIG. 29, an implantable infusion device 110 having an output component 400 is shown. The device depicted in FIG. 29 is similar to the device depicted in, and described with regard to, FIG. 3 above with like numbered components referring to the same or similar components.

Any suitable output components 400 may be employed. For example, the output components 400 may include an audible alarm, a vibration component, or the like to provide the patient sensory feedback that a problem exists or may exist with the infusion system. The output components 400 may include a telemetry component for wirelessly communicating with a device external to the patient to provide a similar warning or to remotely inform a healthcare provider that a problem exists or may exist with the infusion system. Preferably, the nature of the problem (e.g., "catheter complication" is communicated). Alternatively or in addition, a catheter complication event or potential catheter complication event may be stored in memory of the device 110 for later recall by a physician or other clinician when the patient visits the clinic.

Overview of Various Aspects

The present disclosure describes various embodiments of methods, systems, devices and the like for use in detecting catheter status of an implantable infusion system.

In a first aspect, a method for determining status of an implanted catheter includes acquiring raw pressure data from a pressure sensor of an implantable infusion device. The pressure sensor is in communication with a lumen of the catheter operably coupled to the infusion device. The catheter has a delivery region configured to be positioned in a fluid-filled target location of a patient. The delivery region is in communication with the lumen. The method further includes filtering the raw pressure data to remove the DC component, leaving the AC component within a relevant physiological frequency range; rectifying the AC component to produce a rectified pressure signal; calculating a mean magnitude from the integrated rectified signal; and determining whether the mean magnitude is below a predetermined threshold. If the mean magnitude is below the threshold, the catheter is determined to be in a state other than a normal state; i.e. a catheter complication exists or may exist.

A second aspect is a method of the first aspect, wherein calculating the mean magnitude comprises integrating the rectified pressure signal and dividing by the number of samples within the integrated time period.

A third aspect is a method of the first or second aspect, wherein filtering the raw pressure data comprises filtering the data with a band pass filter that has a lower frequency cutoff of between 0.1 Hz and 1 Hz and has an upper frequency cutoff of between 2 Hz and 5 Hz.

A fourth aspect is a method the first or second aspect, wherein filtering the raw pressure data comprises filtering the data with a band pass filter that has a lower frequency cutoff of between 0.2 Hz and 0.5 Hz and has an upper frequency cutoff of between 2 Hz and 3 Hz.

A fifth aspect is a method of the first or second aspect, wherein filtering the raw pressure data comprises filtering the data with a band pass filter that leaves AC data within the frequency range of between 0.5 Hz and 2 Hz.

A sixth aspect is a method of any of the first five aspects, further comprising sampling the raw pressure data prior to the filtering to obtain a pressure reading and obtaining a compensation factor related to sensor gain for the pressure reading, wherein calculating the mean magnitude comprises applying the compensation factor.

A seventh aspect is a method of any of the first six aspects, further comprising determining whether the mean magnitude remains below the predetermined threshold for a predetermined amount of time.

An eighth aspect is a method of the seventh aspect, further comprising determining whether the mean magnitude remains below the predetermined threshold for a predetermined amount of time for a predetermined number of testing cycles.

A ninth aspect is a method of the eighth aspect, further comprising providing an alarm if the mean magnitude is determined to remain below the predetermined threshold for a predetermined amount of time for a predetermined number of testing cycles.

A tenth aspect is a method of any of the first seven aspects, further comprising providing an alarm if the mean magnitude is determined to be below the predetermined threshold.

An eleventh aspect is a method of any of the first ten aspects, further comprising determining whether a sampling frequency period of time has elapsed, wherein the acquiring, filtering, rectifying and calculating steps are commenced if the sampling frequency period of time has elapsed, and wherein the acquiring, filtering, rectifying and calculating steps are not commenced until the sampling frequency period of time has elapsed.

A twelfth aspect is a method of the eleventh aspect, wherein the sampling frequency is between 3 and 96 times per day.

A thirteenth aspect is a method of the eleventh aspect, wherein the sampling frequency is between 6 and 24 times per day.

A fourteenth aspect is a method of the eleventh aspect, further comprising determining whether a sampling window duration has elapsed, wherein if the sample period window has elapsed, the acquiring, filtering, rectifying and calculating steps are stopped.

A fifteenth aspect is a method of the fourteenth aspect, wherein the sampling window duration is between 10 and 60 seconds.

A sixteenth aspect is a method of the fourteenth aspect, wherein the sampling window duration is between 15 and 30 seconds.

A seventeenth aspect is a method of any of the first sixteen aspects, further comprising acquiring patient activity data via an activity sensor and determining whether the patient activity data is indicative of patient activity below a predetermined threshold prior to performing the acquiring, filtering, rectifying and calculating steps.

An eighteenth aspect is a computer readable medium comprising instructions that, when executed by an implantable infusion device, cause the device to carry out a process according to any of the first seventeen aspects.

A nineteenth aspect is an implantable infusion device comprising a pressure sensor configured and positioned to be in communication with a lumen of a catheter configured to be coupled to the infusion device; an analog-to-digital converter for converting raw analog data from the pressure sensor to raw digital data; a band-pass filter for filtering the raw digital data; a rectifier for rectifying the filtered pressure data; an integrator for integrating the filtered pressure data over time; the computer readable medium of the eighteenth aspect; and a processor operably coupled to the pressure sensor, the analog-to-digital converter, the band-pass filter, the rectifier, and the integrator, wherein the processor is configured to execute the instructions of the computer readable medium.

A twentieth aspect is an implantable infusion device comprising a pressure sensor configured and positioned to be in communication with a lumen of a catheter operably couplable to the infusion device; an analog-to-digital converter for converting raw analog data from the pressure sensor to raw digital data; a band-pass filter for filtering the raw digital data; a rectifier for rectifying the filtered pressure data; an integrator for integrating the filtered pressure data over time; electronics configured to calculate an mean magnitude of the integrated pressure data and configured to determine whether the mean magnitude is below a predetermined threshold for identifying a catheter complication or potential catheter complication.

Those skilled in the art will recognize that the preferred embodiments may be altered or amended without departing from the true spirit and scope of the disclosure, as defined in the accompanying claims.

What is claimed is:

1. A method for determining status of an implanted catheter, the method comprising:
    acquiring raw pressure data from a pressure sensor of an implantable infusion device, wherein the pressure sensor is in communication with a lumen of the catheter configured to be coupled to the infusion device, wherein the catheter has a delivery region intended to be positioned in a fluid-filled target location of a patient, the delivery region being in communication with the lumen;
    filtering the raw pressure data to remove the DC component, leaving the AC component within a relevant physiological frequency range;
    rectifying the AC component to produce a rectified pressure signal;
    calculating a mean magnitude of the rectified signal;
    determining whether the mean magnitude is below a predetermined threshold, wherein if the mean magnitude is below the threshold, the catheter is determined to be in a state other than a normal state; and
    determining whether a sampling frequency period of time has elapsed, wherein the acquiring, filtering, rectifying and calculating steps are commenced if the sampling frequency period of time has elapsed, and wherein the acquiring, filtering, rectifying and calculating steps are not commenced until the sampling frequency period of time has elapsed, wherein the sampling frequency is between 3 and 96 times per day.

2. The method of claim 1, wherein calculating the mean magnitude comprises integrating the rectified pressure signal and dividing by the number of samples within the integrated time period.

3. The method of claim 1, wherein filtering the raw pressure data comprises filtering the data with a band pass filter that has a lower frequency cutoff between 0.1 Hz and 1 Hz and has an upper frequency cutoff of between 2 Hz and 5 Hz.

4. The method of claim 1, wherein filtering the raw pressure data comprises filtering the data with a band pass filter that has a lower frequency cutoff of between 0.2 Hz and 0.5 Hz and has an upper frequency cutoff of between 2 Hz and 3 Hz.

5. The method of claim 1, wherein filtering the raw pressure data comprises filtering the data with a band pass filter that leaves AC data within the frequency range of between 0.5 Hz and 2 Hz.

6. The method of claim 1, further comprising sampling the raw pressure data prior to the filtering to obtain a pressure reading and obtaining a compensation factor related to sensor gain for the pressure reading, wherein calculating the mean magnitude comprises applying the compensation factor.

7. The method of claim 1, further comprising determining whether the mean magnitude remains below the predetermined threshold for a predetermined amount of time.

8. The method of claim 7, further comprising determining whether the mean magnitude remains below the predetermined threshold for a predetermined amount of time for a predetermined number of testing cycles.

9. The method of claim 8, further comprising providing an alarm if the mean magnitude is determined to remain below the predetermined threshold for a predetermined amount of time for a predetermined number of testing cycles.

10. The method of claim 1, further comprising providing an alarm if the mean magnitude is determined to be below the predetermined threshold.

11. The method claim 1, wherein the sampling frequency is between 6 and 24 times per day.

12. The method of claim 1, further comprising determining whether a sampling window duration has elapsed, wherein if the sample period window has elapsed, the acquiring, filtering, rectifying and calculating steps are stopped.

13. The method of claim 12, wherein the sampling window duration is between 10 and 60 seconds.

14. The method of claim 12, wherein the sampling window duration is between 15 and 30 seconds.

15. The method of claim 1, further comprising acquiring patient activity data via an activity sensor and determining whether the patient activity data is indicative of patient activity below a predetermined threshold prior to performing the acquiring, filtering, rectifying and calculating steps.

16. A method for determining status of an implanted catheter, the method comprising:
acquiring raw pressure data from a pressure sensor of an implantable infusion device, wherein the pressure sensor is in communication with a lumen of the catheter configured to be coupled to the infusion device, wherein the catheter has a delivery region intended to be positioned in a fluid-filled target location of a patient, the delivery region being in communication with the lumen;
filtering the raw pressure data to remove the DC component, leaving the AC component within a relevant physiological frequency range;
rectifying the AC component to produce a rectified pressure signal;
calculating a mean magnitude of the rectified signal;
determining whether the mean magnitude is below a predetermined threshold, wherein if the mean magnitude is below the threshold, the catheter is determined to be in a state other than a normal state; and
determining whether a sampling frequency period of time has elapsed, wherein the acquiring, filtering, rectifying and calculating steps are commenced if the sampling frequency period of time has elapsed, and wherein the acquiring, filtering, rectifying and calculating steps are not commenced until the sampling frequency period of time has elapsed; and
determining whether a sampling window duration has elapsed, wherein if the sample period window has elapsed, the acquiring, filtering, rectifying and calculating steps are stopped.

17. A method for determining status of an implanted catheter, the method comprising:
acquiring raw pressure data from a pressure sensor of an implantable infusion device, wherein the pressure sensor is in communication with a lumen of the catheter configured to be coupled to the infusion device, wherein the catheter has a delivery region intended to be positioned in a fluid-filled target location of a patient, the delivery region being in communication with the lumen;
filtering the raw pressure data to remove the DC component, leaving the AC component within a relevant physiological frequency range;
rectifying the AC component to produce a rectified pressure signal;
calculating a mean magnitude of the rectified signal;
determining whether the mean magnitude is below a predetermined threshold, wherein if the mean magnitude is below the threshold, the catheter is determined to be in a state other than a normal state; and
acquiring patient activity data via an activity sensor and determining whether the patient activity data is indicative of patient activity below a predetermined threshold prior to performing the acquiring, filtering, rectifying and calculating steps.

18. A method for determining status of an implanted catheter, the method comprising:
acquiring raw pressure data from a pressure sensor of an implantable infusion device, wherein the pressure sensor is in communication with a lumen of the catheter configured to be coupled to the infusion device, wherein the catheter has a delivery region intended to be positioned in a fluid-filled target location of a patient, the delivery region being in communication with the lumen;
filtering the raw pressure data to remove the DC component, leaving the AC component within a relevant physiological frequency range;
rectifying the AC component to produce a rectified pressure signal;
calculating a mean magnitude of the rectified signal;
determining whether the mean magnitude is below a predetermined threshold, wherein if the mean magnitude is below the threshold, the catheter is determined to be in a state other than a normal state;
determining whether the mean magnitude remains below the predetermined threshold for a predetermined amount of time;
determining whether the mean magnitude remains below the predetermined threshold for a predetermined amount of time for a predetermined number of testing cycles; and
providing an alarm if the mean magnitude is determined to remain below the predetermined threshold for a predetermined amount of time for a predetermined number of testing cycles.

19. A method for determining status of an implanted catheter, the method comprising:
acquiring raw pressure data from a pressure sensor of an implantable infusion device, wherein the pressure sensor is in communication with a lumen of the catheter configured to be coupled to the infusion device, wherein the catheter has a delivery region intended to be positioned in a fluid-filled target location of a patient, the delivery region being in communication with the lumen;

filtering the raw pressure data to remove the DC component, leaving the AC component within a relevant physiological frequency range;

rectifying the AC component to produce a rectified pressure signal;

calculating a mean magnitude of the rectified signal;

determining whether the mean magnitude is below a predetermined threshold, wherein if the mean magnitude is below the threshold, the catheter is determined to be in a state other than a normal state; and providing an alarm if the mean magnitude is determined to be below the predetermined threshold.

\* \* \* \* \*